US007250389B1

(12) United States Patent
Sakanaka et al.

(10) Patent No.: US 7,250,389 B1
(45) Date of Patent: Jul. 31, 2007

(54) ANTIFUNGAL COMPOUND AND PROCESS FOR PRODUCING THE SAME

(75) Inventors: Osamu Sakanaka, Odawara (JP); Koichi Mitomo, Odawara (JP); Takayoshi Tamura, Odawara (JP); Yasushi Murai, Odawara (JP); Katsuharu Iinuma, Odawara (JP); Takeshi Teraoka, Yokohama (JP); Kikuko Kuzuhara, Yokohama (JP); Haruki Mikoshiba, Yokohama (JP); Makoto Taniguchi, Kishiwada (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/601,655

(22) PCT Filed: Feb. 8, 1999

(86) PCT No.: PCT/JP99/00541

§ 371 (c)(1),
(2), (4) Date: Aug. 4, 2000

(87) PCT Pub. No.: WO99/40081

PCT Pub. Date: Aug. 12, 1999

(30) Foreign Application Priority Data

Feb. 6, 1998 (JP) ................................ 10-026257

(51) Int. Cl.
*A01N 504/14* (2006.01)
*C07D 405/00* (2006.01)

(52) U.S. Cl. .................... 504/140; 544/374; 546/281.7

(58) Field of Classification Search ................ 549/267; 514/450, 254.1, 336; 546/282.4, 281.7; 544/353, 544/354, 374

See application file for complete search history.

(56) References Cited

FOREIGN PATENT DOCUMENTS

| | | |
|---|---|---|
| JP | 44-235 | 1/1969 |
| JP | 7-196489 | 8/1995 |
| JP | 7-233165 | 9/1995 |

OTHER PUBLICATIONS

Hanafi, et al., "UK-2A, B, C and D, novel antifungal antibiotics from Streptomyces sp. 517-02. II. Structural elucidation", J. Antibiot., 49 (12), 1226-1231, 1996.*

Shimano et al., "Total Synthesis of the Antifungal Dilactones UK-2A and UK-3A: The Determination of their Relative and Absolute Configurations, Analog Synthesis and Antifungal Activities", Tetrahedron 54, pp. 12745-12774, 1998.*

Shimano et al., "Enantioselective Total Synthesis of the Antifungal Dilactone, UK-2A: The Determination of the Relative and Absolute Configurations.", Tetrahedron Letters 39, 4363-4366, 1996.*

"UK-3A, a Novel Antifungal Antibiotic from *Streptomyces sp.* 517-02: Fermentation, Isolation, Structural Elucidation and Biological Properties", Ueki et al., The Journal of Antibiotics, vol. 50, No. 7.*

Ueki et al. "The Mode of Action of UK-2A and UK-3A, Novel Antifungal Antibiotics"The Journal of Antibiotics vol. 50, No 12 pp. 1052-1057, (1997).

Shimano et al., "Total Synthesis of the Antifungal Dilaotones UK-2A and UK-3A: The Determination of th r relative and Absolute Configurations, Analog Synthesis and Antifungal Activities.", Tetrahedron 54 (1998) 12745-12774.

Ueki et al., "UK-3A, a novel antifungal antibiotic from *Streptomyces sp.* 517-02: fermentation, isolation, structural elucidation and biological properties", Journal of Antibotics (1997). 50(7), 551-555.

Ueki et al., "UK-2A, B, C and D, novel antifungal antibiotics from *Streptomyces sp.* 517.02.1. Fermentation, isolation, and biological properties", Journal of Antibiotics (1996), 49(7), 639-643.

Hanafi et al., "The structures of UK-1 and UK-2, novel antibiotics from *Streptomyces sp.* 517.02", Tennen Yuki Kagobutsu Toronkai Koen Yoshihsu (1994), 36th, 728-35.

* cited by examiner

*Primary Examiner*—D. Margaret Seaman
*Assistant Examiner*—Binta Robinson
(74) *Attorney, Agent, or Firm*—Wenderoth, Lind & Ponack, L.L.P.

(57) ABSTRACT

Disclosed are novel compounds useful for prevention or control of diseases derived from fungi, a process for producing the same, and novel antifungal agents using the novel compounds. The compounds useful for prevention and treatment of diseases derived from fungi according to the present invention include novel compounds represented by formula (I). The compounds represented by formula (I) have potent antifungal activity against diseases derived from fungi, and do not have phytotoxicity to mammals and agricultural and garden plants, from which diseases should be eliminated, and, even when applied to agricultural and garden plants, have high photostability.

(I)

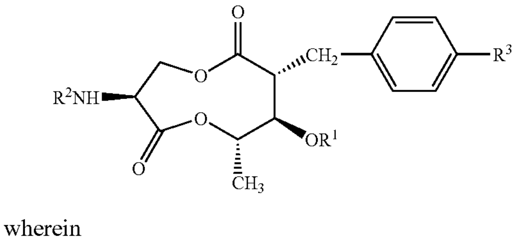

wherein $R^1$ represents isobutyryl, tigloyl, isovaleryl, or 2-methylbutanoyl;

$R^2$ represents a hydrogen atom, an aromatic carboxylic acid residue, or a protective group of amino; and $R^3$ represents a hydrogen atom, nitro, amino, acylamino, or N,N-dialkylamino, excluding the case where, when $R^1$ represents isobutyryl, tigloyl, isovaleryl, or 2-methylbutanoyl with $R^3$ representing a hydrogen atom, $R^2$ represents a 3-hydroxypicolinic acid residue, 3-hydroxy-4-methoxypicolinic acid residue, or a 3,4-dimethoxypicolinic acid residue.

17 Claims, No Drawings

ANTIFUNGAL COMPOUND AND PROCESS FOR PRODUCING THE SAME

This application is a 371 application of PCT/JP99/00541 filed Feb. 8, 1999.

BACKGROUND OF THE INVENTION

1. Field of the Invention

The present invention relates to a novel compound or a salt thereof having antifungal activity, a process for producing the same, and use thereof.

2. Background Art

Various diseases induced by fungi have seriously injured the health of human beings and non-human animals and have brought about serious damage to crops. For this reason, provision of compounds having antifungal activity and antifungal agents comprising these compounds as active ingredients and provision of advantageous processes for producing these compounds have always been desired in the art.

For example, some fungi are pathogenic to human beings and non-human animals and have been regarded as being responsible for fungal infectious diseases. The pathogenicity of fungi is on the whole weak. However, fungi often bring about grave condition in patients having lowered resistance thereto. This has led to an expectation of the development of novel pharmaceuticals useful for the treatment of these diseases. Some fungi are known as being pathogenic, and the development of novel antifungal agents for agricultural and gardening applications has been required associated with the control of plant diseases. Further, in reflection of recent housing circumstances, the invasion of filamentous fungi into housing has become an issue. In particular, the invasion of filamentous fungi often brings about such conditions as an allergy to human beings. The development of antifungal agents for preventing the occurrence of such symptoms, particularly the development of novel fungicides, has been desired in the art.

With a view to overcoming these problems, various antifungal agents have been developed with certain success.

However, the development of antifungal agents, which are not only environmentally friendly but also are safe against human beings and non-human animals and plants and are highly effective, has been desired in the art. Regarding agricultural and garden plants, the development of antifungal agents, which have high antifungal activity and excellent photostability, has been particularly desired.

On the other hand, Japanese Patent Laid-Open No. 233165/1995 discloses a part of compounds represented by formula (II). Compounds represented by formula (II) are generally referred to as "UK-2."

(II)

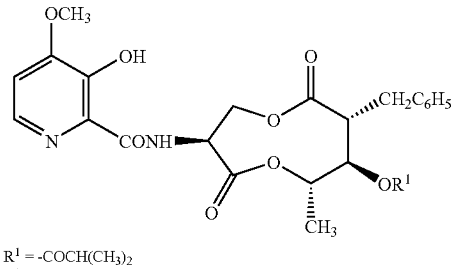

UK2A $R^1$ = $-COCH(CH_3)_2$
UK2B $R^1$ = $-COC(CH)_3 = CHCH_3$
UK2C $R^1$ = $-COCH_2CH(CH_3)_2$
UK2D $R^1$ = $-COCH(CH_3)CH_2CH_3$ wherein $R^1$ represents a straight-chain or branched saturated aliphatic hydrocarbon group or unsaturated aliphatic hydrocarbon group.

For example, Japanese Patent Laid-Open No. 233165/1995 discloses, in working examples, compounds represented by formula (II) wherein $R^1$ represents isobutyryl (hereinafter referred to as "UK-2A"), compounds represented by formula (II) wherein $R^1$ represents tigloyl (hereinafter referred to as "UK-2B"), compounds represented by formula (II) wherein $R^1$ represents an isovaleryl group (hereinafter referred to as "UK-2C"), and compounds represented by formula (II) wherein $R^1$ represents 2-methylbutanoyl (hereinafter referred to as "UK-2D").

The above laid-open publications describe that UK-2 has antifungal activity and is useful as an active ingredient of antifungal agents for medical applications, fungicides for agricultural and gardening applications, and fungicides for industrial applications.

In particular, as compared with antimycins which likewise have a dilactone structure with a nine-membered ring and are represented by formula (III), UK-2 has the same or higher antimicrobial activity against fungi including yeasts, such as *Candida*, and filamentous fungi, such as *Aspergillus, Penicillium, Mucor, Cladosporium, Rhizopus*, Sclerotina, and *Trichoderma*, and has much lower cytotoxicity against culture cells, such as P388. Therefore, UK-2 has led to an expectation for usefulness thereof.

(III)

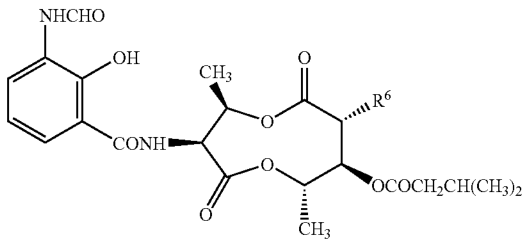

Antimycin A $R^6$ = $-(CH_2)_5CH_3$
Antimycin $A_3$ $R^6$ = $-(CH_2)_3CH_3$

Further, the above laid-open publications describe the isolation of UK-2 as fermentation products from microorganisms belonging to Streptoverticillium.

Furthermore, "Tetrahedron Letters 39 (1998) 4363-4366", discloses the synthesis of UK-2.

SUMMARY OF THE INVENTION

The present inventors have now found that novel compounds prepared from UK-2 as a starting compound have potent antifungal activity against diseases derived from fungi, do not have any phytotoxicity against mammals and agricultural and garden plants, from which diseases should be eliminated, and, also when used in agricultural and garden plants, can exhibit high photostability. The present invention has been made based on such finding.

Accordingly, it is an object of the present invention to provide a novel compound useful for the prevention and control of diseases derived from fungi, a process for producing the same, and a novel antifungal agent using the novel compound.

The compound according to the present invention is represented by formula (I):

(I)

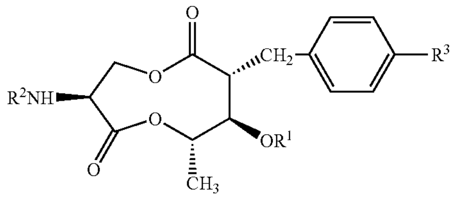

wherein $R^1$ represents isobutyryl, tigloyl, isovaleryl, or 2-methylbutanoyl;

$R^2$ represents a hydrogen atom, an aromatic carboxylic acid residue, or a protective group of amino; and $R^3$ represents a hydrogen atom, nitro, amino, acylamino, or N,N-dialkylamino, excluding the case where, when $R^1$ represents isobutyryl, tigloyl, isovaleryl, or 2-methylbutanoyl with $R^3$ representing a hydrogen atom, $R^2$ represents a 3-hydroxypicolinic acid residue, 3-hydroxy-4-methoxypicolinic acid residue, or a 3,4-dimethoxypicolinic acid residue.

DETAILED DESCRIPTION OF THE INVENTION

Deposit of Microorganism

*Streptoverticillium* sp. SAM 208 strain, a microorganism for producing the compound represented by formula (II), is deposited under FERM BP-6446 with National Institute of Bioscience and Human-Technology, Agency of Industrial Science & Technology (1-3, Higashi 1-chome, Tukuba-shi, Ibaraki-ken, Japan). The depositor of the microorganism is Suntory Ltd. (1-40, Dojimahama 2-chome, Kita-ku, Osaka-shi, Japan). The original deposit thereof is Acceptance No. FERM P-14154 dated Feb. 17, 1994, and the date of receipt of the request for transfer to deposit based on Budapest Treaty is Aug. 3, 1998.

Definition

As used herein, the term "alkyl or alkoxy" as a group or a part of a group means straight-chain or branched alkyl or alkoxy. The term "halogen" used herein means fluorine, chlorine, bromine, or iodine.

Compound Represented by Formula (I)

In the formula (1), $R^1$ represents isobutyryl, tigloyl, isovaleryl, or 2-methylbutanoyl;

$R^2$ represents a hydrogen atom, an aromatic carboxylic acid residue, or a protective group of amino; and $R^3$represents a hydrogen atom, nitro, amino, acylamino, or N,N-dialkylamino, excluding the case where, when $R^1$ represents isobutyryl, tigloyl, isovaleryl, or 2-methylbutanoyl with $R^3$ representing a hydrogen atom, $R^2$ represents a 3-hydroxypicolinic acid residue, 3-hydroxy-4-methoxypicolinic acid residue, or a 3,4-dimethoxypicolinic acid residue.

The aromatic carboxylic acid residue represented by $R^2$ is preferably an aromatic heterocyclic carboxylic acid residue or a benzoic acid residue (that is, benzoyl). Specific examples of aromatic heterocyclic carboxylic acid residues include picolinic acid residue, nicotinic acid residue, 4-quinolinecarboxylic acid residue, 5-pyrimidinecarboxylic acid residue, 2-quinoxalinecarboxylic acid residue.

One or more hydrogen atoms on the aromatic rings of these aromatic carboxylic acid residues may be substituted. Specific examples of substituents usable herein include: hydroxyl; halogen atoms; nitro; amino; di $C_{1-6}$ alkylamino (preferably dimethylamino); formylamino; $C_{1-6}$ alkyl (preferably $C_{1-4}$ alkyl, more preferably methyl or ethyl); $C_{1-6}$ alkoxy (preferably $C_{1-4}$ alkoxy, more preferably methoxy or ethoxy); benzyloxy; $C_{1-10}$ aliphatic acyloxy wherein one or more hydrogen atoms on the alkyl of the aliphatic acyloxy may be substituted, for example, by carboxyl, benzyloxycarbonyl, $C_{1-4}$ alkyloxycarbonyl, or benzyloxycarbonylamino; benzoyloxy; $C_{1-4}$ alkyloxycarbonyloxy; $(C_{1-4})$ alkyloxycarbonyl$(C_{1-4})$ alkyloxy; p-nitrobenzyloxycarbonyl $(C_{1-4})$ alkyloxy; $C_{1-6}$ alkylsulfonyloxy; di $(C_{1-6})$ alkylphosphoryloxy; and diphenylphosphoryloxy.

Specific examples of preferred aromatic carboxylic acid residues include:

(1) hydroxybenzoic acid residue (preferably 2-hydroxybenzoic acid residue);

(2) picolinic acid residue substituted by at least one substituent selected from the group consisting of hydroxy, $C_{1-6}$ alkoxy (preferably $C_{1-4}$ alkoxy, more preferably methoxy or ethoxy), benzyloxy, $C_{1-6}$ alkylcarbonyloxy (preferably $C_{1-4}$alkylcarbonyloxy, more preferably acetyloxy or propionyloxy with the alkyl portion thereof being optionally substituted by benzyloxycarbonylamino), benzoyloxy, $c_{1-6}$ alkoxycarbonyloxy (preferably $C_{1-4}$ alkoxycarbonyloxy), $C_{1-6}$ alkyloxycarbonyl $C_{1-10}$ alkylcarbonyloxy (preferably $C_{1-4}$ alkyl (more preferably methyl or ethyl)oxycarbonyl $C_{1-10}$ alkyl(preferably $C_{1-8}$ alkyl, more preferably $C_{1-6}$ alkyl) carbonyloxy), benzyloxycarbonyl $C_{1-10}$ alkylcarbonyloxy, carboxy $C_{1-10}$ alkyl (preferably $C_{1-6}$alkyl) carbonyloxy, $C_{1-6}$ alkylphosphoryloxy, di$(C_{1-6})$alkylphosphoryloxy, and diphenylphosphoryloxy;

(3) hydroxy-substituted nicotinic acid residue (preferably 2-hydroxynicotinic acid residue);

(4) quinolinecarboxylic acid residue (preferably 4-quinolinecarboxylic acid residue) substituted by at least one substituent selected from the group consisting of hydroxy and $C_{1-6}$ alkyl (preferably $C_{1-4}$ alkyl, more preferably methyl or ethyl);

(5) hydroxy-substituted pyrimidinecarboxylic acid residue (preferably 4-hydroxy-5-pyrimidinecarboxylic acid residue); and (6) hydroxy-substituted quinoxalinecarboxylic acid residue (preferably 3-hydroxy-2-quinoxalinecarboxylic acid residue).

According to a preferred embodiment of the present invention, the hydroxybenzoic acid residue (1) may be substituted by one or more substituents. Examples of substituents usable herein include nitro, amino, di $C_{1-6}$ alkyl amino (preferably di $C_{1-4}$ alkyl amino, more preferably methyl or ethyl), formylamino, halogen atom, and $C_{1-6}$ alkoxy (preferably $C_{1-4}$ alkoxy, more preferably methoxy or ethoxy).

Further, according to a preferred embodiment of the present invention, examples of more preferred picolinic acid residues (2) include those substituted by $C_{1-6}$alkoxy (most preferably methoxy). Examples of more preferred picolinic acid residues include those substituted by $C_{1-6}$alkoxy and, in addition, by hydroxy, $C_{1-6}$alkylcarbonyloxy, benzoyloxy, $C_{1-6}$ alkoxycarbonyloxy, $C_{1-6}$ alkyloxycarbonyl $C_{1-10}$ alkylcarbonyloxy, benzyloxycarbonyl $C_{1-10}$ alkylcarbonyloxy, carboxy $C_{1-10}$ alkylcarbonyloxy, di ($C_{1-6}$) alkylphosphoryloxy, or diphenylphosphoryloxy. Especially preferred is a picolinic acid residue having $C_{1-6}$ alkoxy at its 4-position and, in addition, other substituent, noted above, at its 3-position.

The protective. group of amino represented by $R^2$ refers to, among conventional protective groups of amino, one which can be removed under reduction conditions or by acid treatment. Preferred protective groups of amino include, for example, benzyloxycarbonyl, p-nitrobenzyloxycarbonyl, methoxycarbonyl, t-butyloxycarbonyl. A more preferred protective group of amino is benzyloxycarbonyl.

Examples of the acyl in the acyl amino represented by $R^3$ include $C_{1-6}$ saturated and unsaturated aliphatic acyl (preferably formyl, acetyl, and propionyl), aromatic acyl (preferably, optionally substituted benzoyl, for example, benzoyl, p-methoxybenzoyl, and p-nitrobenzoyl). A particularly preferred acyl is formyl.

Examples of the alkyl in the N,N-dialkylamino represented by $R^3$ include $C_{1-4}$ alkyl(preferably methyl and ethyl).

Among the compounds represented by formula (I) according to the present invention, a preferred group of compounds include a group of compounds represented by formula (I) wherein $R^1$ represents isobutyryl, tigloyl, isovaleryl, or 2-methylbutanoyl, $R^2$ represents a hydrogen atom, an aromatic carboxylic acid residue, or a protective group of amino, and $R^3$ represents a hydrogen atom. Another preferred group of compounds include a group of compounds represented by formula (I) wherein $R^1$ represents isobutyryl, tigloyl, isovaleryl, or 2-methylbutanoyl, $R^2$ represents picolinyl having hydroxy at its 3-position and methoxy at its 4-position, $R^3$ represents nitro, amino, acylamino, or N,N-dialkylamino.

A further preferred group of compounds include: compounds represented by formula (I) wherein $R^1$ represents isobutyryl, tigloyl, isovaleryl, or 2-methylbutanoyl, $R^2$ represents picolinyl having acyloxy at its 3-position and methoxy at its 4-position, picolinyl having acetoxy at its 3-position and methoxy at its 4-position, picolinyl having di($C_{1-6}$) alkylphosphoryloxy at its 3-position and methoxy at its 4-position, or picolinyl having diphenylphosphoryloxy at its 3-position and methoxy at its 4-position, and $R^3$ represents a hydrogen atom; and compounds represented by formula (I) wherein $R^1$ represents isobutyryl, tigloyl, isovaleryl, or 2-methylbutanoyl, $R^2$ represents picolinyl having hydroxy at its 3-position and methoxy at its 4-position, and $R^3$ represents formylamino or N,N-dimethylamino.

In these preferred group of compounds, protection of hydroxyl in 3-hydroxy-4-methoxypicolinyl residue by acyl can offer excellent antimicrobial activity possessed by UK-2 and, at the same time, can significantly improve the photostability of the compounds per se.

According to another embodiment of the present invention, the compounds of formula (I) may be present in a salt form.

The compounds represented by the formula (I) may be present in the form of salts. Examples of salts include pharmacologically acceptable salts, and specific examples thereof include lithium, sodium, potassium, magnesium, and calcium salts; salts with ammonium and suitable non-toxic amines, for example, $C_{1-6}$ alkylamine (for example, triethylamine) salts, $C_{1-6}$ alkanolamine (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl- , β-phenethylamine, N,N-dibenzylethylenediamine, or dibenzylamine) salts, and heterocyclic amines (for example, morpholine or N-ethylpyridine) salts; salts of hydrogen halides such as hydrofluoric acid, hydrochloric acid, hydrobromic acid and hydroiodic acid; inorganic acid salts such as sulfate, nitrate, phosphate, perchlorate and carbonate; salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid; salts of amino acids such as arginic acid, aspartic acid and glutamic acid; and salts of organic acids such as methanesulfonic acid and p-toluenesulfonic acid.

Production of Compounds Represented by Formula (I)

The compounds represented by formula (I) may be produced by various chemical reactions using UK-2 as a starting compound. Thus, according to another aspect of the present invention, there is provided a process for producing a compound represented by formula (I) or a salt thereof.

The present inventors have repeatedly made the following studies with a view to producing more useful novel derivatives using as a starting compound UK-2 having the above great features, which has led to the completion of the present invention.

In UK-2, a nine-membered lactone ring moiety is attached to a substituted pyridine ring moiety through a carboxylic acid amido bond. The present inventors have succeeded in obtaining a nine-membered ring lactone having an amino group by chemically cleaving the carboxylic acid amido bond. This amino compound may be used as an important intermediate for the production of UK-2 derivatives. The present inventors have further succeeded in producing novel compounds useful as antimicrobial agents by condensing the above amino compound with an aromatic carboxylic acid different from UK-2.

The carboxylic acid amido bond may be generally chemically cleaved by hydrolysis with an acid or an alkali. This method, however, requires treatment with a highly concentrated acid or alkali at a high temperature for a long period of time, and hence can be applied to only compounds wherein portions other than the reaction site are stable against acids or alkalis. UK-2 has three carboxylic ester bonds including the nine-membered lactone ring structure, and these bonds are easily cleaved under such hydrolysis conditions.

Trimethyloxonium tetrafluoroborate $(CH_3)_3OBF_4$ is frequently used as a chemical reagent for cleaving the carboxylic acid amido bond, in the compound having a very sensitive functional group, without damage to the other portions (Tetrahedron Letters, 1549, (1967)).

First of all, the present inventors also have applied this method to UK-2. However, the reaction did not substantially proceed, and only UK-2 of the starting compound was obtained containing a very small amount of decomposition products.

On the other hand, iminoetherification through iminochloride is known as a method for cleaving the carboxylic acid amido bond at the 6- and 7-positions respectively in penicillins and cephalosporins having a β-lactam ring which is highly susceptible to hydrolysis with acids and alkalis. Specifically, at the outset, treatment with a chlorinating agent, such as phosphorus pentachloride, is carried out to give a corresponding iminochloride. The iminochloride is treated with a lower alcohol, such as methanol, to produce an imino ether which is finally treated with water to cleave the acyl group, thereby obtaining a free amino compound at a high yield.

The present inventors have applied this iminoetherification method to UK-2 and, as a result as described below, have succeeded in obtaining the desired amino derivative. The production of the amino derivative from UK-2 by the iminoetherification method is first success in compounds having a chemically very unstable nine-membered dilactone ring structure, such as UK-2 and antimycins.

According to a preferred embodiment of the present invention, the compounds represented by formula (I) may be produced by the following process.

(1) Starting Compound:

UK-2 may be used as the starting compound for the compounds represented by formula (I). UK-2 may be obtained from microorganisms belonging to Streptoverticillium.

The microorganisms belonging to Streptoverticillium may be obtained by separating *Actinomyces* (ray fungus) from microorganism separation sources, such as soil, according to a conventional method and then selecting, from these strains, strains which can produce compounds represented by formula (II).

An example of fungi capable of producing compounds represented by formula (II) is a ray fungus designated as *Streptoverticillium* sp. SAM 2084 described above in connection with the deposit of microorganism.

UK-2, a compound represented by formula (II), may be isolated from a culture or a culture solution of the microorganism SAM 2084 according to a method described in Japanese Patent Laid-Open No. 233165/1995.

(2) Chemical cleaving of carboxylic acid amido bond between nine-membered lactone ring moiety and substituted pyridine ring moiety:

According to one embodiment of the present invention, UK-2 amino derivatives may be produced by chemical cleaving of the carboxylic acid amido bond in UK-2. Further, it is possible to produce compounds represented by formula (I) wherein $R^1$ is as defined above, $R^2$ represents a hydrogen atom or a protective group of amino, and $R^3$ represents a hydrogen atom, nitro, or N,N-dialkylamino. According to one embodiment of the present invention, UK-2 as the starting compound is dissolved in an inert organic solvent, a chlorinating agent is added to the solution, and the mixture is heated under reflux to perform a reaction. The amount of the chlorinating agent added is 1 to 10 molar equivalents, preferably 2 to 3 molar equivalents. The reaction time is 1 to 5 hr, preferably 1 to 3 hr. The reaction temperature is 0 to 80° C., preferably 30 to 40° C.

This reaction gives a corresponding iminochloro compound. After the completion of the reaction, the reaction solution is cooled to −30 to −20° C. To the cooled reaction solution is added a lower alcohol (cooled to 0 to 5° C.) of weight of 10 to 100 times that of UK-2 as the starting compound, followed by a reaction. The reaction time is 1 to 15 hr, preferably 2 to 3 hr. The reaction temperature is 0 to 50° C., preferably 15 to 25° C. This gives a corresponding iminoether compound. The iminoether compound easily undergoes hydrolysis by treatment with water to produce a desired amino derivative of UK-2. This chemical reaction is represented by chemical reaction formula 1 below.

A representative example of the chlorinating agent used is phosphorus pentachloride.

Lower alcohols usable herein include straight-chain or branched alcohols, for example, methanol, ethanol, n-propyl alcohol, isopropyl alcohol, n-butyl alcohol, and isobutyl alcohol.

A free amino group and a dilactone structure are copresent in the amino derivative having nine-membered dilactone ring thus obtained. Therefore, this compound is likely to be decomposed. Therefore, isolation and storage for a long period of time in this form pose a problem.

For this reason, preferably, the desired UK-2 amino derivative in its free amino group is converted to a salt, for example, p-toluenesulfonate or hydrochloride, or is protected by a protective group which can be easily introduced and removed, for example, benzyloxycarbonyl, p-nitrobenzyloxycarbonyl, methoxycarbonyl, or t-butyloxycarbonyl. The treated product obtained is purified and isolated, and, in this state, is stored. In this case, preferably, the salt or the protected amino group is returned to the free amino group immediately before use or within the reaction system, and is then used in the condensation.

According to another embodiment of the present invention, a corresponding amino compound and an amino protected compound thereof can be obtained by the above reaction also from a compound, obtained by a process described below, represented by formula (1) wherein $R^1$ is as defined above, $R^2$ represents an aromatic carboxylic acid residue, and $R^3$ represents nitro or N,N-dialkylamino.

Chemical Reaction Formula 1:

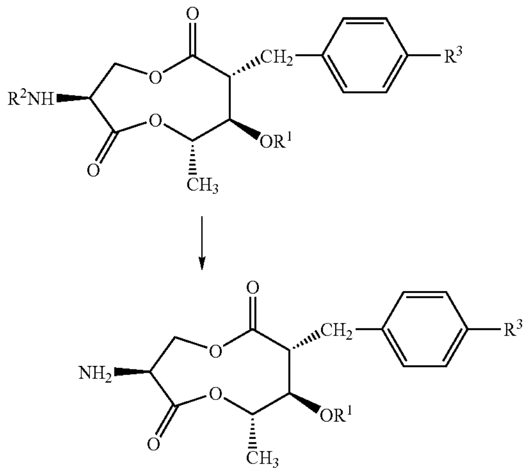

Amino Derivative of UK-2

(3) Product ion of compounds represented by formula (I) by acylation:

According to one embodiment of the present invention, the amino derivative of UK-2 obtained by the above process is easily reacted with any aromatic carboxylic acid, aromatic carboxylic acid chloride, aromatic carboxylic anhydride, active ester of aromatic carboxylic acid or the like.

This reaction can give a compound represented by formula (I) wherein $R^1$ is as defined above, $R^1$ represents an aromatic carboxylic acid residue, and $R^3$ represents a hydrogen atom.

For example, the amino derivative of UK-2 and an aromatic carboxylic acid may be treated with a dehydration condensation reagent in an inert solvent to conduct an ester condensation, thereby producing a corresponding compound having an aromatic carboxylic acid residue represented by formula (I).

Dehydration condensation reagents usable herein include, for example, dicyclohexylcarbodiimide, 1-ethyl-3-(3-dimethylaminopropyl)carbodiimide hydrochloride, and a combination of dicyclohexylcarbodiimide with 1-hydroxybenzotriazole.

When an aromatic carboxylic acid compound, whose reactivity has been activated in advance, such as an aromatic carboxylic acid chloride, an aromatic carboxylic anhydride, or an active ester of an aromatic carboxylic acid, is used, it is possible to use, for example, a method wherein the aromatic carboxylic acid is treated with thionyl chloride, phosphorus pentachloride or the like to give an acid chloride, a method wherein the aromatic carboxylic acid is reacted with a chlorocarbonic ester, phosphorus oxychloride or the like to give an acid anhydride, or a method wherein the aromatic carboxylic acid is condensed with N-hydroxysuccinimide or 2-mercaptobenzothiazole to give an active ester.

The compound represented by formula (I) as the contemplated aromatic carboxylic acid amide may be easily produced by reacting the activated aromatic carboxylic acid with the amino derivative of UK-2 in an inert solvent under neutral or weakly basic conditions.

According to another embodiment of the present invention, in the same manner as described above, a corresponding aromatic carboxylic acid amide compound may be obtained from the compound represented by formula (I) wherein $R^1$ is as defined above, $R^2$ represents a hydrogen atom, $R^3$ represents nitro, acylamino, or N,N-dialkylamino.

These carboxylic acid amides have been demonstrated to have high antifungal activity, no phytotoxicity against various plant diseases, and excellent prophylactic or therapeutic effect. Heterocyclic carboxylic acid derivatives with a hydroxyl group being present in a carbon atom adjacent to a carbon atom attached to the amido group and, in addition, having at least one nitrogen atom as the ring-constituting atom, and salicylic acid derivatives which have been unsubstituted or substituted at 3- or 5-position by a nitrogen-containing group (such as nitro, formylamino, or N,N-dimethylamino), or chloro had particularly high activity.

(4) Acylation of hydroxyl group in aromatic carboxylic acid residue represented by $R^2$:

According to one embodiment of the present invention, a compound represented by formula (I), wherein $R^1$ and $R^2$ are as defined above and $R^2$represents an aromatic carboxylic acid residue having an acyloxy group as a substituent, may be produced by the following method.

UK-2 or a compound represented by formula (I), wherein $R^1$ and $R^3$ are as defined above and $R^2$ represents an aromatic carboxylic acid residue having a hydroxyl group as a substituent, is used as a starting compound (compound A). The starting compound at its hydroxyl group is acylated. The acylation substantially quantitatively yields a corresponding compound represented by formula (I) wherein the hydroxyl group in the aromatic carboxylic acid residue represented by $R^2$ has been acylated (compound B; —$COR^4$ represents a $C_{1-6}$ saturated or unsaturated aliphatic acyl group or aromatic acyl group). This chemical reaction is as represented by chemical reaction formula 2.

Most methods for acylation of hydroxyl groups may be applied to acylation used in the present invention. For example, a combination of an acid anhydride of benzoic acid, a $C_{1-6}$ saturated or unsaturated aliphatic carboxylic acid, an aromatic carboxylic acid or the like (for example, acetic anhydride, propionic anhydride, or benzoic acid) with a tertiary organic base, such as pyridine or triethylamine, a combination of a corresponding acid chloride (for example, acetyl chloride, propionyl chloride, pivaloyl chloride, or benzoyl chloride) with the tertiary organic base, or a combination of a corresponding free carboxylic acid, an amino acid with the amino group being protected or the like with a dehydration condensation agent, such as dicyclohexylcarbodiimide is useful in the absence or presence of an inert solvent, such as methylene chloride, chloroform, 1,4-dioxane, or tetrahydrofuran.

Chemical Reaction Formula 2:

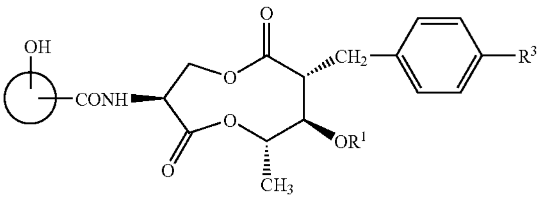

Compound A

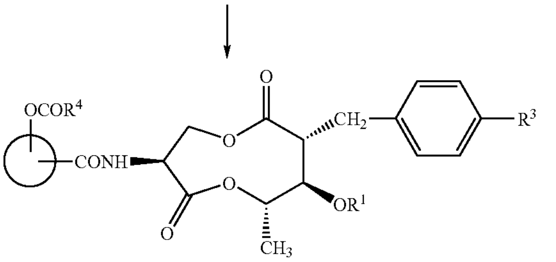

Compound B

According to a further embodiment of the present invention, the compound A may be reacted with a dicarboxylic acid dichloride ($ClCO(CH_2)_nCOCl$ wherein n is an integer of 2 or more) typified by succinic acid dichloride, pimelic acid dichloride or the like.

In this case, a reaction of the compound A with a one molar equivalent or a slightly excess amount of chloride can efficiently produce a monochloride compound (compound C).

A subsequent reaction of the compound C, without isolation and purification, with an alcohol ($R^5OH$ wherein $R^5$ represents a substituted or unsubstituted benzyl or $C_{1-4}$ alkyl) in the presence of a suitable base can produce a corresponding ester compound (compound D).

Alcohols usable herein include, for example, primary alcohols, such as methanol, ethanol, and benzyl alcohol, and, in addition, secondary alcohols, such as isopropanol, and tertiary alcohols, such as t-butyl alcohol.

The compound D thus obtained may be converted to compound E of free carboxylic acid type by deesterification depending upon the nature of the ester.

In particular, when the compound D is a benzyl ester compound (wherein $R^5$ represents $CH_2C_6H_5$) or a p-nitrobenzyl ester (wherein $R^5$ represents $CH_2C_6H_4$-p-$NO_2$) the deesterification may be easily carried out by conventional catalytic hydrogenation without detriment to functional groups in its molecule. This advantageously permits the production of compound E having a carboxyl group. This chemical reaction is as represented by chemical reaction formula 3.

Chemical Reaction Formula 3:

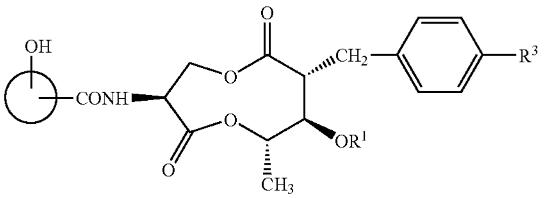

Compound A

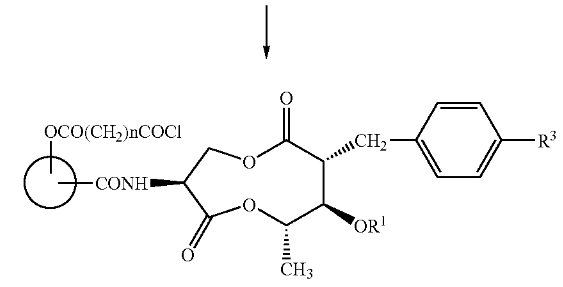

Compound C

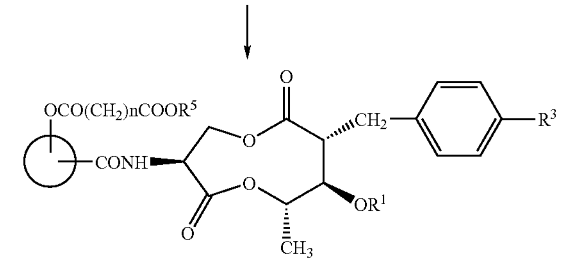

Compound D

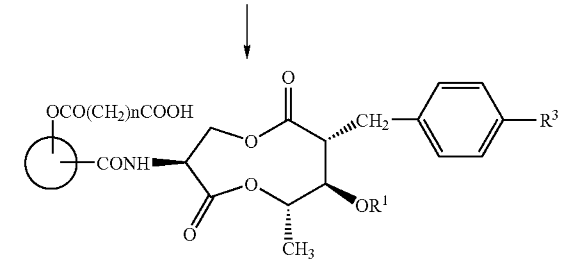

Compound E

The acyl compounds obtained by the above reaction according to the present invention (compounds B, D, and E) have high antifungal activity possessed by UK-2 and, at the same time, the photostability has been improved by virtue of acylation. Thus, they have properties which are favorable as agricultural chemicals for use in outdoor farms and the like.

(5) Phosphorylation of hydroxyl group in aromatic carboxylic acid residue represented by $R^2$:

According to one embodiment of the present invention, a compound represented by formula (I) wherein $R^1$ and $R^3$ are as defined above and $R^2$ represents an aromatic carboxylic acid residue having a phosphoryloxy group as a substituent (compound F wherein $R^6$ represents $C_{1-6}$ alkyl or phenyl) may be also produced by the following process.

According to a preferred embodiment of the present invention, UK-2 or a compound represented by formula (I) wherein $R^1$ and $R^3$ are as defined above and $R^2$ represents an aromatic carboxylic acid residue having a hydroxyl group as a substituent (compound A) in its hydroxyl group is phosphorylated. The phosphorylation can provide a corresponding compound represented by formula (I) wherein the hydroxyl group in the aromatic carboxylic acid residue represented by $R^2$ has been phosphorylated (compound F) at a high yield. This chemical reaction is as represented by chemical reaction formula 4.

Most conventional phosphorylation methods may be applied to the phosphorylation used in the present invention. For example, the phosphorylation may be carried out by a reaction using a phosphoric diester monochloride (such as diphenyl phosphate chloride or diethyl phosphate chloride) in an inert solvent, such as methylene chloride, chloroform, 1,4-dioxane, or tetrahydrofuran, in the presence of a tertiary organic base, such as pyridine or triethylamine. According to the present invention, dimethylaminopyridine may be added as a reaction accelerator.

Chemical Reaction Formula 4:

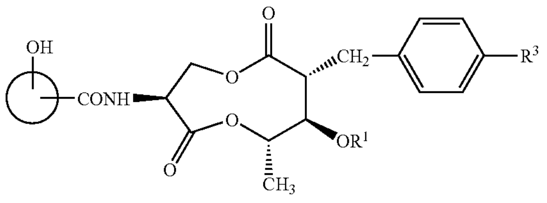

Compound A

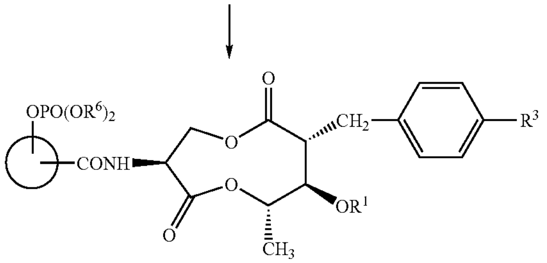

Compound F (6) Chemical modification of benzene ring in benzyl group:

According to one embodiment of the present invention, a compound represented by formula (I), wherein $R^1$ is as defined above, $R^2$ represents an aromatic carboxylic acid residue, and $R^3$ represents nitro, amino, acylamino, or N,N-dialkylamino, may be produced by the following chemical reaction (modification).

According to a preferred embodiment of the present invention, among the compounds obtained by the process (2) or (3) (for example, compound A), a compound wherein $R^3$ represents a hydrogen atom (compound G) is used as a starting compound. The benzene ring in the benzyl group in the compound G is subjected to electrophilic nitro substitution on the aromatic ring. This nitro substitution can produce compound H wherein a nitro group has been selectively introduced into para position of the benzene ring in the compound G without decomposition (a compound represented by formula (I) wherein $R^1$ is as defined above, $R^2$ represents an aromatic carboxylic acid residue, and $R^3$represents nitro) in a high yield.

The nitration used in the present invention may be carried out by a conventional method. According to the present invention, the nitration is preferably carried out using fuming nitric acid as strong nitration agent in cooled (−20° C. to −50° C.) methylene chloride or chloroform solvent. The nitration time is preferably one to two hr.

According to another embodiment of the present invention, a chemical conversion method commonly used for normal aromatic nitro compounds may be applied to the resultant compound H. For example, the compound H may be reduced by a conventional method to give an amino compound (compound I).

The compound I thus obtained may be subjected to conventional N-acylation (such as formylation or acetylation) or N-alkylation (such as N,N-dimethylation or N,N-diethylation). These reactions provide compounds represented by formula (I) wherein $R^1$ is as defined above, $R^2$ represents an aromatic carboxylic acid residue, and $R^3$ represents an amino group (compound I), an acylamino group (compound J in the case of formylation), or N,N-dialkylamino group (compound K in the case of dimethylation). These chemical reactions are as represented by chemical reaction formula 5.

Chemical Reaction Formula 5:

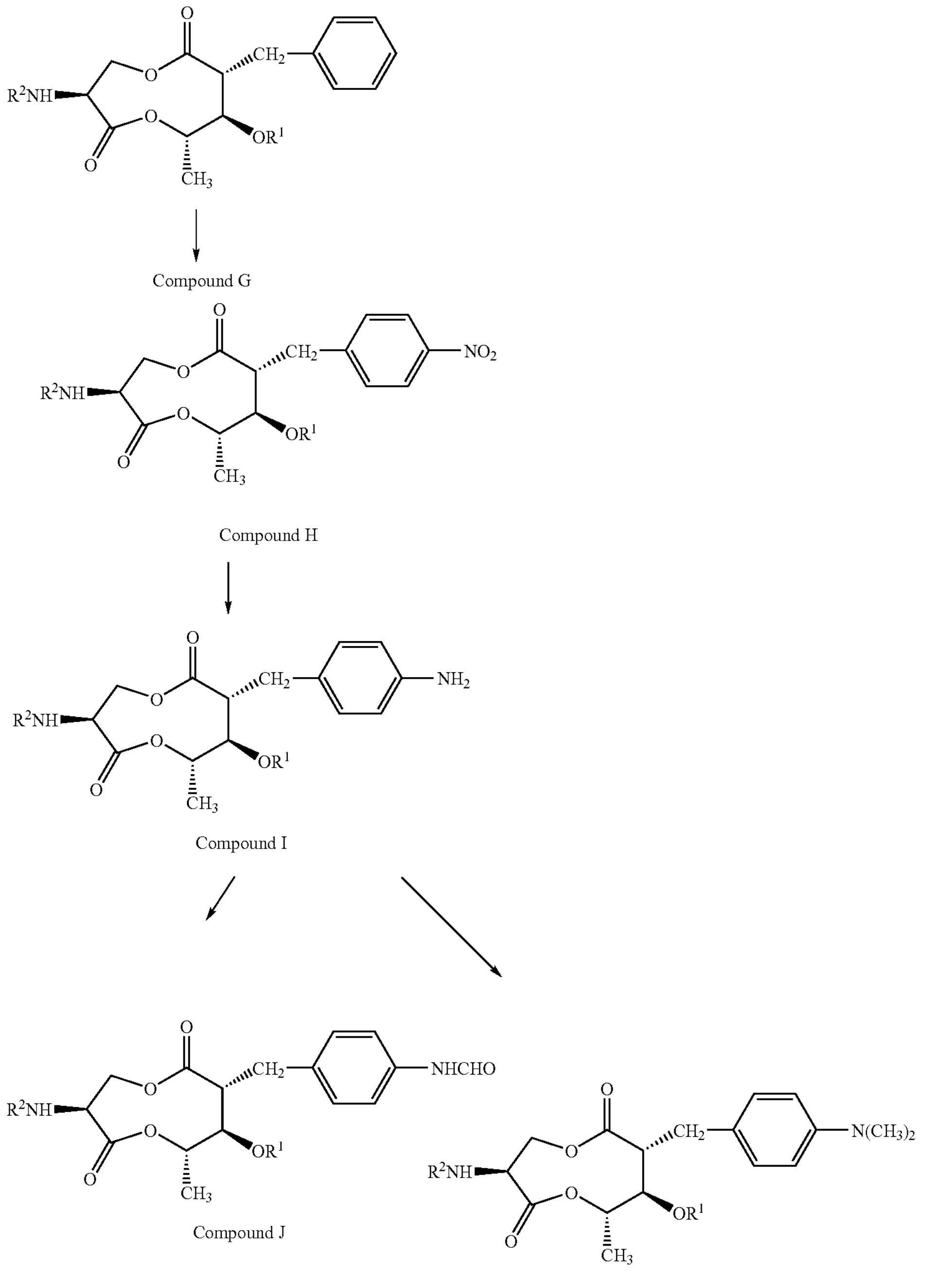

Compound G

Compound H

Compound I

Compound J

Compound K

Use of Compounds Represented by Formula (I)/Pharmaceutical Compositions

The first aspect of the present invention is based on the fact that the compounds represented by formula (I) have potent antifungal activity against diseases derived from fungi, and do no have any phytotoxicity against human beings and non-human animals and agricultural and garden plants which are objects regarding the prevention and control of diseases.

Specifically, the compounds represented by formula (I), produced using UK-2 as a starting compound via chemical reactions described below, have potent antifungal activity against fungi and have properties as antifungal agents, particularly as active ingredients of medical antifungal agents, fungicides for agricultural and gardening applications and fungicides for industrial applications.

The compounds represented by formula (I) according to the present invention have potent antifungal activity and excellent prophylactic or therapeutic effect for various plant diseases. Therefore, the compounds represented by formula (I) are useful as active ingredients of antifungal agents for the treatment of fungal infectious diseases derived from fungi sensitive to the compounds of the present invention and, in addition, as active ingredients of antifungal agents for agricultural and gardening applications and antifungal agents for industrial applications.

Antifungal agents comprising as an active ingredient the compound represented by formula (I) according to the present invention may be administered to human beings and non-human animals through any one of dosage routes, for example, oral or parenteral routes, such as subcutaneous administration, intravenous injection, intramuscular injection, rectal administration, or percutaneous administration.

Antifungal agents, for the treatment of fungal infectious diseases, comprising as an active ingredient the compound represented by formula (I) according to the present invention are preferably provided as suitable dosage forms depending on dosage routes.

For example, they are preferably formed into preparations mainly including injections such as intravenous injections or intramuscular injections, oral preparations such as capsules, tablets, granules, powders, pills, grains or troches, preparations for local administration, such as ointments, lotions, and pessaries, rectal preparations, oily suppositories or aqueous suppositories.

In order to more surely attain the antifungal effect, preferably, these preparations are produced by selecting and combining pharmacologically acceptable additives, such as excipients, extenders, binders, humidifiers, disintegrating agents, surface active agents, lubricants, dispersants, buffers, preservatives, dissolution aids, corrigents, analgesic agents or stabilizers.

The aforementioned acceptable and non-toxic additives include, for example, lactose, fructose, glucose, starch, gelatin, magnesium carbonate, synthetic magnesium silicate, talc, magnesium stearate, methylcellulose, carboxymethylcellulose or a salt- thereof, gum arabic, polyethylene glycol, syrup, vaseline, glycerin, ethanol, propylene glycol, citric acid, sodium chloride, sodium sulfite, and sodium phosphate.

Preferably, the dose of the antifungal agent comprising the compound represented by formula (I) according to the present invention is properly determined in each case by taking into consideration symptoms, ages, sex and the like.

Therefore, desirably, the dose of therapeutic agents or prophylactic agents comprising the compound represented by formula (I) according to the present invention, especially contraceptives or therapeutic agents for breast carcinoma or ovarian carcinoma, is generally about 0.01 to 1,000 mg, preferably 0.1 to 100 mg per day to an adult patient for intravenous administration. For intramuscular administration, desirably, the dose is generally about 0.01 to 1000 mg, preferably 0.1 to 100 mg, per day per adult. For oral administration, desirably, the dose is generally about 0.5 to 2000 mg, preferably 1 to 1000 mg per day per adult. For any of these types of administration, the dose may be administered in one or more portions per day.

Antifungal agents for agricultural and gardening applications comprising the compound represented by formula (I) according to the present invention are preferably provided as suitable dosage forms depending on various dosage routes by using carriers suitable for various dosage forms and, if necessary, incorporating proper additives. For example, they are preferably formed into solid preparations, such as powders, grains, and granules, and liquid preparations, such as solutions, medicinal oils, emulsions, wettable powders, suspensions, and aerosols. Preferably, the liquid preparations are properly diluted before use.

Preferable carries usable herein include: solid powder or particulate carriers, such as clay, talc, diatomaceous earth, white clay, calcium carbonate, silicic anhydride, bentonite, sodium sulfate, silica gel, salts of organic acids, saccharides, starch, resins, and synthetic or naturally occurring polymers; and liquid carriers, for example, aromatic hydrocarbons, such as xylene, aliphatic hydrocarbons, such as kerosene, ketones, such as methyl ethyl ketone, cyclohexanone, and isophorone, lactams, ethers, such as anisole, alcohols, such as ethanol, propanol, and ethylene glycol, esters, such as ethyl acetate and butyl acetate, dimethylsulfoxide, dimethylformamide, and water.

In order to more surely attain the effect of the preparations, preferably, these preparations are used in combination with additives properly selected, depending upon applications, from emulsifiers, dispersants, wetting agents, binders, and lubricants.

Additives usable herein include, for example, nonionic and ionic surfactants, carboxymethylcellulose, polyvinyl acetate, polyvinyl alcohol, gums, salts of stearate, waxes, and sizing agents.

In the antifungal agent for agricultural and gardening applications according to the present invention, the compound represented by formula (I) is generally incorporated in an amount of about 0.01 to 10% by weight, preferably about 0.1 to 5% by weight, for powders, in an amount of about 1 to 90% by weight, preferably about 5 to 75% by weight, for wettable powders, in an amount of about 0.01 to 40% by weight, preferably about 0.1 to 20% by weight, for grains, in an amount of about 1 to 60% by weight, preferably about 5 to 40% by weight, for liquid preparations, and in an amount of about 1 to 80% by weight, preferably about 5 to 50% by weight, for suspensions.

The antifungal agent for agricultural and gardening applications according to the present invention may be, of course, used alone or in combination with or as a mixture thereof with agricultural chemicals, such as bactericides, insecticides, herbicides, and growth-regulating substances of plants, or fertilizer or soil conditioners.

Preferably, the amount of the antifungal agent applied for agricultural and gardening applications according to the present invention is properly determined by taking into consideration dosage forms, application methods, purposes, and application times. Specifically, in general, the amount of the antifungal agent applied is preferably 10 to 2000 g per ha, more preferably 50 to 1000 g per ha, in terms of the amount of the compound represented by formula (I) as the active ingredient.

The antifungal agent for agricultural and gardening applications according to the present invention may be applied to agricultural and garden plants, as well as to growing environment (for example, enclosure) and equipment for agricultural and gardening applications.

The compound represented by formula (I) according to the present invention, when intended to be used as antifungal agents for industrial applications, may be formed, in combination with conventional carriers and, if necessary, conventional assistants, into suitable preparations depending upon various dosage forms. These antifungal agents for industrial applications prevent the propagation of harmful fungi which pose a problem in general industrial products and in the course of the production of these products to prevent contamination with harmful fungi. Examples of antifungal agents for industrial applications contemplated in the present invention include fungicides for the prevention of surface contamination of wood, countermeasuring agents for rotting fungi in wood products, preservatives/fungicides to be added to paints, wall coverings, and fungicides to be added in polymer processing, and fungicides to be used in processing of leather, fibers, and textiles.

EXAMPLES

Example 1

(1)(2R,3R,4S,7S)-7-Amino-2-benzyl-5,9-dioxa-3-iso-butyryloxy-4-methyl-1,6-cyclononanedione; and (2) p-toluenesulfonate thereof UK-2A (500 mg) was dissolved in 50 mL of methylene chloride. Pyridine (0.15 mL) and 395 mg of phosphorus pentachloride were added to the solution under ice cooling. The mixture was heated under reflux for 1.5 hr. The reaction solution was cooled to −30° C. Thereafter, 50 mL of methanol, which had been previously cooled to 0° C., was added to the reaction solution, and a reaction was allowed to proceed for 15 hr. Methylene chloride (200 mL) and 150 mL of saturated aqueous sodium hydrogencarbonate, which had been previously cooled to 0° C., were added thereto, followed by separation. The aqueous layer was extracted twice with 20 mL of dichloromethane. The combined organic layers were dried over magnesium sulfate, and concentrated under the reduced pressure. The residue was dissolved in 50 mL of ethyl acetate. A solution of 180 mg of p-toluenesulfonic acid monohydrate in ethyl acetate (50 mL ) was added to the solution at room temperature. The precipitated p-toluenesulfonate (2) was collected by filtration. The amount of the product thus obtained was 232 mg (yield 45%).

This p-toluenesulfonate (2) (87 mg) was dissolved in a mixed solution composed of methylene chloride and 5% aqueous sodium hydrogencarbonate, followed by separation. The organic layer was dried over sodium sulfate, and concentrated under the reduced pressure to obtain 51 mg (yield 86%) of the title compound (1).

Title Compound (1)

$^1$H-NMR ($CD_3OD$): δ=1.22 (6H, d, J=7.0, CH($\underline{CH_3}$)$_2$), 1.32 (3H, d, J=6.1, 4-$CH_3$), 2.60 (1H, septet, J=7.0, $\underline{CH}$($CH_3$)$_2$), 2.76 (1H, dd, J=13.4, 4.3, $C_6H_5\underline{CH_2}$), 2.81 (1H, dd, J=13.4, 9.5, $C_6H_5\underline{CH_2}$), 3.02 (1H, td, J=4.3, 9.5, H-2), 3.82 (1H, bs, H-8), 4.41, 4.51 (each 1H, each bs, $NH_2$), 4.70-5.30 (4H, m, H-3, 4, 7, 8), 7.11-7.23 (5H, m, $C_6H_5$)

MS (EI): m/z=363(M)

p-Toluenesulfonate (2)

$^1$H-NMR (($CD_3$)$_2$SO): δ=1.17 (6H, d, J=7.0, CH($\underline{CH_3}$)$_2$), 1.32 (3H, d, J=5.86, 4-$CH_3$), 2.30 (3H, s, $\underline{CH_3}C_6H_4SO_3H$), 2.60-2.80 (3H, m, J=7.0, $\underline{CH}$($CH_3$)$_2$, $C_6H_5\underline{CH_2}$), 3.00-3.20 (1H, m, H-2), 3.50(1H, bs, H-8), 4.52(1H, dd, J=5.5, 8.4, H-8), 4.90-5.20 (3H, m, H-3, 4, 7), 7.11 (2H, d, J=7.6, $CH_3\underline{C_6H_4}SO_3H$), 7.14-7.30 (5H, m, $C_6H_5$), 7.48 (2H, d, J=8.1, $CH_3\underline{C_6H_4}SO_3H$)

Example 2

(2R,3R,4S,7S)-7-Amino-2-benzyl-5,9-dioxa-3-isobutyryloxy-4-methyl-1,6-cyclononanedione tosylate The title compound (yield 41%) was obtained in the same manner as in Example 1, except that isobutanol was used instead of methanol.

Example 3

(2R,3R,4S,7S)-7-Benzyloxycarbonylamino-2-benzyl-5,9-dioxa-3-isobutyryloxy-4-methyl-1,6-cyclononanedione UK-2A (100 mg) was dissolved in 10 mL of methylene chloride. Pyridine (32 mg) and 83 mg of phosphorus pentachloride were added to the solution under ice cooling. The mixture was heated under reflux for 1.5 hr. Next, the reaction solution was cooled to −30° C. Methanol (10 mL), which had been previously cooled to 0° C., was added thereto, and a reaction was allowed to proceed at room temperature for 3 hr. Methylene chloride (50 mL) and 50 mL of saturated aqueous sodium hydrogencarbonate, which had been previously cooled to 0° C., were added to the reaction solution, followed by separation. The aqueous layer was extracted twice with 20 ml of methylene chloride. The combined organic layers were dried over magnesium sulfate, and then concentrated under the reduced pressure. The residue was dissolved in 5 mL of methylene chloride. Pyridine (46 μl) and 84 μl of benzyloxycarbonyl chloride were added to the solution under ice cooling, and a reaction was allowed to proceed at room temperature for 20 min. The reaction solution was concentrated under the reduced pressure. The residue was purified by column chromatography on silica gel (hexane:ethyl acetate=3:1) to obtain 45 mg (yield 48%) of the title compound.

$^1$H-NMR ($CDCl_3$): δ=1.23 (6H, d, J=6.8, CH($\underline{CH_3}$)$_2$), 1.29 (3H, d, J=6.2, 4-$CH_3$), 2.50-2.80 (2H, m, $\underline{CH}$($CH_3$)$_2$, $C_6H_5\underline{CH_2}$), 2.80-3.00 (2H, m, $C_6H_5\underline{CH_2}$, H-2), 3.45 (1H, bs, H-8), 4.80-5.00 (2H, m, H-4, 7), 5.09 (2H, s, $C_6H_5\underline{CH_2}$OCO), 5.00-5.30 (2H, m, H-3, 8), 5.45 (1H, d, J=7.8, CONH), 7.09-7.33 (10H, m, $C_6H_5$×2)

MS (EI): m/z=497(M)

Example 4

(2R,3R,4S,7S)-7-(2-Hydroxynicotinylamino)-2-benzyl-5,9-dioxa-3-isobutyryloxy-4-methyl-1,6-cyclononanedione The compound (2) (40 mg) obtained in Example 1, 20 mg of 2-hydroxynicotinic acid, and 20 mg of 1-hydroxybenzotriazole were dissolved in 2 mL of pyridine. A solution of 29 mg of 1-ethyl-3-(3'-dimethylaminopropyl)carbodiimide hydrochloride in tetrahydrofuran (THF, 2 mL) was added to the solution, and a reaction was allowed to proceed at room temperature for 3 hr. Methylene chloride and water were added to the reaction solution, followed by separation. The organic layer was dried over magnesium sulfate, and then concentrated under the reduced pressure. The residue was purified by column chromatography on silica gel (ethyl acetate:hexane =4: 1) to obtain 28 mg (yield 78%) of the title compound.

$^1$H-NMR ($CDCl_3$): δ=1.24 (6H, d, J=7.0, CH(<u>$CH_3$</u>)$_2$), 1.32 (3H, d, J=6.2, 4-$CH_3$), 2.58-2.73 (2H, m, <u>CH</u>($CH_3$)$_2$, $C_6H_5$<u>$CH_2$</u>), 2.89-3.05 (2H, m, H-2, $C_6H_5$<u>$CH_2$</u>), 3.63(1H, bs, H-8), 4.94-5.00 (1H, m, H-4), 5.18-5.25 (2H, m, H-3, H-7), 5.40(1H, bs, H-8), 6.55 (1H, t, J=6.8, H-5'), 7.12-7.29 (5H, m, $C_6H_5$), 7.63 (1H, dd, J=6.8, 2.2, H-4'), 8.57 (1H, dd, J=6.8, 2.2, H-6'), 10.31 (1H, d, CONH, J=6.8), 12.78 (1H, s, OH)

MS (TSP): m/z=485(M+H)

Example 5

(2R,3R,4S,7S)-7-(6-Hydroxypicolinylamino)-2-benzyl-5,9-dioxa-3-isobutyryloxy-4-methyl-1,6-cyclononanedione The title compound (yield 52%) was obtained in the same manner as in Example 4, except that 6-hydroxypicolinic acid was used instead of 2-hydroxynicotinic acid.

$^1$H-NMR ($CDCl_3$): δ=1.05-1.34 (9H, m, CH(<u>CH</u>)$_2$, 4-$CH_3$), 2.60-2.75 (2H, m, <u>CH</u>($CH_3$)$_2$, $C_6H_5$<u>$CH_2$</u>), 2.87-3.05 (2H, m, H-2, $C_6H_5$<u>$CH_2$</u>), 3.73 (1H, bs, H-8), 4.46 (1H, d, OH, J=8.9), 4.94-5.00 (1H, m, H-4), 5.18-5.32 (3H, m, H-3, 7, 8), 6.78 (1H, d, J=8.9, aromatic (pyridine ring)), 7.12-7.30 (8H, m, aromatic (pyridine ring, $C_6H_5$)), 7.58 (1H, dd, J=7.0, 2.2, aromatic (pyridine ring)), 8.18 (1H, d, J=7.3, CONH,)

MS (TSP): m/z=485 (M+H)

Example 6

(2R,3R,4S,7S)-7-(2,4-Dihydroxypyrimidine-5-carboxyl-amino)-2-benzyl-5,9-dioxa-3-isobutyryloxy-4-methyl-1,6-cyclononanedione The title compound (yield 23%) was obtained in the same manner as in Example 4, except that 2,4-dihydroxypyrimidine-5-carboxylic acid was used instead of 2-hydroxynicotinic acid.

$^1$H-NMR ($CDCl_3$): δ=1.05-1.32 (9H, m, 4-$CH_3$, CH(<u>$CH_3$</u>)$_2$), 2.59-2.72 (2H, m, <u>CH</u>($CH_3$)$_2$, $C_6H_5$<u>$CH_2$</u>), 2.90-3.00 (2H, m, H-2, $C_6H_5$<u>$CH_2$</u>), 3.60 (1H, bs, H-8), 4.22 (1H, bd, OH), 4.90-5.40 (4H, m, H-3, 4, 7, 8), 7.11-7.26 (8H, m, $C_6H_5$), 8.51 (1H, s, aromatic (pyrimidine ring)), 9.29 (1H, d, J=7.3, CONH)

MS (TSP): m/z=502(M+H)

Example 7

(2R,3R,4S,7S)-7-(3-Hydroxy-2-methylquinoline-4-carboxylamino)-2-benzyl-5,9-dioxa-3-isobutyryloxy-4-methyl-1,6-cyclononanedione The title compound (yield 12%) was obtained in the same manner as in Example 4, except that 3-hydroxy-2-methyl-4-quinolinecarboxylic acid was used instead of 2-hydroxynicotinic acid.

$^1$H-NMR ($CDCl_3$): δ=1.20-1.40 (9H, 4-$CH_3$, CH(<u>$CH_3$</u>)$_2$), 2.77 (3H, s, $CH_3$(quinoline)), 4.80-5.40 (4H, m, H-3, 4, 7, 8), 6.80-8.00 (10H, m, aromatic), 11.34 (1H, s, OH)

MS (TSP): m/z=549 (M+H)

Example 8

(2R,3R,4S,7S)-7-(3-Hydroxy-2-quinoxalinecarboxylamino)-2-benzyl-5,9-dioxa-3-isobutyryloxy-4-methyl-1,6-cyclononanedione The title compound (yield 27%) was obtained in the same manner as in Example 4, except that 3-hydroxy-2-quinoxalinecarboxylic acid was used instead of 2-hydroxynicotinic acid.

$^1$H-NMR ($CDCl_3$): δ=1.23-1.37 (9H, m, J=7.1, 1.1, CH(<u>$CH_3$</u>)$_2$, 4-$CH_3$), 2.60-2.75 (2H, m, <u>CH</u>($CH_3$)$_2$, $C_6H_5$ <u>$CH_2$</u>), 2.90-3.10 (2H, m, H-2, $C_6H_5$<u>$CH_2$</u>), 3.66 (1H, bs, H-8), 4.99-5.51 (4H, m, H-3, 4, 7, 8), 7.13-8.12 (10H, m, CONH, aromatic (benzene ring)), 11.78 (1H, s, OH)

MS (TSP): m/z=536 (M+H)

Example 9

(2R,3R,4S,7S)-7-(3,6-Dihydroxypicolinylamino)-2-benzyl-5,9-dioxa-3-isobutyryloxy-4-methyl-1,6-cyclononanedione The title compound (yield 22%) was obtained in the same manner as in Example 4, except that 3,6-dihydroxypicolinic acid was used instead of 2-hydroxynicotinic acid.

$^1$H-NMR ($CDCl_3$): δ=1.23 (6H, m, J=2.5, 6.8, CH(<u>$CH_3$</u>)$_2$), 1.33 (3H, d, J=6.3, 4.—$CH_3$), 2.60-2.73 (2H, m, <u>CH</u>($CH_3$)$_2$, $C_6H_5$<u>$CH_2$</u>), 2.90-3.05 (2H, m, H-2, $C_6H_5$<u>$CH_2$</u>), 3.70 (1H, bs, H-8), 4.93-4.99 (1H, m, H-4), 5.13-5.25 (3H, m, H-3, 7, 8), 6.82 (1H, d, J=5.4, H-5'), 7.12-7.30 (5H, m, $C_6H_5$), 7.33 (1H, d, J=5.4, H-6'), 8.49 (1H, d, J=8.4, CONH), 11.35 (1H, s, OH)

MS (TSP): m/z=501(M+H)

Example 10

(2R,3R,4S,7S)-7-(3-Benzyloxy-4,6-dimethoxypicolinyl-amino)-2-benzyl-5,9-dioxa-3-isobutyryloxy-4-methyl-1,6-cyclononanedione The title compound (yield 92%) was obtained in the same manner as in Example 4, except that 3-benzyloxy-4,6-dimethoxypicolinic acid was used instead of 2-hydroxynicotinic acid.

$^1$H-NMR($CDCl_3$): δ=1.22 (6H, dd, J=1.6, 7.3, CH(<u>$CH_3$</u>)$_2$), 1.30 (3H, d, J=6.8, 4-$CH_3$), 2.60-2.72 (2H, m, $C_6H_5$<u>$CH_2$</u>, <u>CH</u>($CH_3$)$_2$), 2.90-3.00 (2H, m, H-2, $C_6H_5$<u>$CH_2$</u>), 3.49 (1H, bs, H-8), 3.32, 3.92 (each 3H, each s, 4'-OCH3, 6'-$OCH_3$), 4.90-5.00 (1H, m, H-4), 5.10 (2H, s, $C_6H_5$<u>$CH_2$</u>O), 5.18-5.30 (3H, m, H-3, 7, 8), 6.33 (1H, s, H-5'), 7.12-7.50 (10H, m, <u>$C_6H_5$</u>$CH_2$, <u>$C_6H_5$</u>$CH_2$O), 8.34 (1H, d, J=8.4, CONH)

MS (TSP): m/z=635(M+H)

Example 11

(2R,3R,4S,7S)-7-(3-Benzyloxy-4,5-dimethoxypicolinyl-amino)-2-benzyl-5,9-dioxa-3-isobutyryloxy-4-methyl-1,6-cyclononanedione The title compound (yield 97%) was obtained in the same manner as in Example 4, except that 3-benzyloxy-4,5-dimethoxypicolinic acid was used instead of 2-hydroxynicotinic acid.

$^1$H-NMR($CDCl_3$): δ=1.23 (6H, dd, J=1.6, 7.3, CH(<u>$CH_3$</u>)$_2$), 1.31 (3H, d, J=6.8, 4-$CH_3$), 2.60-2.72 (2H, m, $C_6H_5\underline{CH_2}$, $\underline{CH}(CH_3)_2$), 2.90-3.00 (2H, m, H-2, $C_6H_5\underline{CH_2}$), 3.49 (1H, bs, H-8), 3.96, 3.99 (each 3H, each s, 4'-OCH3, 5'-$OCH_3$), 4.90-5.00 (1H, m, H-4), 5.10 (2H, S, $C_6H_5\underline{CH_2}O$), 5.18-5.30 (3H, m, H-3, 7, 8), 7.12-7.52 (10H, m, $\underline{C_6H_5}CH_2$, $\underline{C_6H_5}CH_2O$), 8.06 (1H, s, H-6'), 8.31 (1H, d, J=8.4, CONH)

MS (TSP): m/z=635(M+H)

Example 12

(2R,3R,4S,7S)-7-(3-Hydroxy-4,6-dimethoxypicolinylamino)-2-benzyl-5,9-dioxa-3-isobutyryloxy-4-methyl-1,6-cyclononanedione To 64 mg of the compound obtained in Example 10 was added 7 mg of 10% palladium-carbon. The air in the system was replaced by nitrogen, and 30 mL of methanol was added thereto. Further, the atmosphere in the system was replaced by hydrogen, and a reaction was allowed to proceed with vigorous stirring. One hr after the initiation of the reaction, the catalyst was removed by filtration. Further, the catalyst was washed with 1 N hydrochloric acid. Extraction with methylene chloride was carried out. The extract was dried over magnesium sulfate, and then concentrated under the reduced pressure to give 5.0 mg (yield 9.2%) of the title compound.

$^1$H-NMR ($CDCl_3$): δ=1.23 (6H, dd, J=1.6, 7.3, $CH(\underline{CH_3})_2$), 1.33 (3H, d, J=6.8, 4-$CH_3$), 2.60-2.72 (2H, m, $C_6H_5\underline{CH_2}$, $\underline{CH}(CH_3)_2$), 2.90-3.00 (2H, m, H-2, $C_6H_5\underline{CH_2}$), 3.58 (1H, bs, H-8), 3.89 (6H, s, 4'-$OCH_3$, 6'-$OCH_3$), 4.90-5.00 (1H, m, H-4), 5.10-5.40 (3H, m, H-3, 7, 8), 6.30 (1H, s, H-5'), 7.11-7.33 (5H, m, $\underline{C_6H_5}CH_2$), 8.35 (1H, d, J=8.4, CONH), 11.44 (1H, s, 3'-OH)

MS (TSP): m/z=545 (M+H)

Example 13

(2R,3R,4S,7S)-7-(3-Hydroxy-4,5-dimethoxypicolinylamino)-2-benzyl-5,9-dioxa-3-isobutyryloxy-4-methyl-1,6-cyclononanedione The title compound (yield 45%) was obtained in the same manner as in Example 12, except that the compound obtained in Example 11 was used instead of the compound obtained in Example 10.

$^1$H-NMR ($CDCl_3$): δ=1.23 (6H, dd, J=1.6, 7.3, $\underline{CH}(\underline{CH_3})_2$), 1.33 (3H, d, J=6.8, 4-$CH_3$), 2.60-2.72 (2H, m, $C_6H_5\underline{CH_2}$, $\underline{CH}(CH_3)_2$), 2.80-3.00 (2H, m, H-2, $C_6H_5CH_2$), 3.58 (1H, bs, H-8), 3.98, 4.03 (each 3H, each s, 4'-$OCH_3$, 5'-$OCH_3$), 4.90-5.00 (1H, m, H-4), 5.10-5.40 (3H, m, H-3, 7, 8), 7.11-7.27 (5H, m, $\underline{C_6H_5}CH_2$), 7.81 (1H, s, H-6'), 8.37 (1H, d, J=8.4, CONH), 11.70 (1H, s, 3'-OH)

MS (TSP): m/z=545 (M+H)

Example 14

(2R,3R,4S,7S)-7-(3-Benzyloxy-4-methoxypicolinylamino)-2-benzyl-5,9-dioxa-3-isobutyryloxy-4-methyl-1,6-cyclononanedione The compound (500 mg) obtained in Example 13 was dissolved in 25 mL of acetone. Anhydrous potassium carbonate (134 mg) and 136 μl of benzyl bromide were added sequentially to the solution. The mixture was heated at 60° C. for 3 hr. The solvent was removed by distillation under the reduced pressure. The residue was purified by column chromatography on silica gel (hexane:ethyl acetate=1:1) to give 319 mg (yield 39%) of the title compound.

$^1$H-NMR ($CDCl_3$): δ=1.23 (6H, dd, J=1.6, 7.3, $CH(\underline{CH_3})_2$), 1.31 (3H, d, J=6.8, 4-$CH_3$), 2.58-2.71 (2H, m, $C_6H_5\underline{CH_2}$, $\underline{CH}(CH_3)_2$), 2.88-3.02 (2H, m, H-2, $C_6H_5\underline{CH_2}$), 3.52 (1H, bs, H-8), 3.91 (3H, s, 4'-$OCH_3$), 4.90-5.00 (1H, m, H-4), 5.10 (2H, s, $C_6H_5\underline{CH_2}O$), 5.18-5.35 (3H, m, H-3, 7, 8), 6.94 (1H, d, J=5.4, H-5'), 7.12-7.52 (10H, m, $\underline{C_6H_5}CH_2$, $\underline{C_6H_5}CH_2O$), 8.25 (1H, d, J=5.4, H-6'), 8.38 (1H, d, J=8.4, CONH)

MS (TSP): m/z=605 (M+H)

Example 15

(2R,3R,4S,7S)-7-(3-Benzyloxy-4-methoxypicolinylamino-N-oxide)-2-benzyl-5,9-dioxa-3-isobutyryloxy-4-methyl-1,6-cyclononanedione The compound (315 mg) obtained in Example 14 was dissolved in 15 mL of methylene chloride. m-Perbenzoic acid (70%) (385 mg) was added to the solution, and a reaction was allowed to proceed at room temperature for 5 hr. The reaction solution was washed first with 5% aqueous sodium hydrogencarbonate and then with a 10% aqueous sodium thiosulfate solution. The solvent was removed by distillation under the reduced pressure. The residue was purified by column chromatography on silica gel (chloroform:methanol =20 : 1-10 : 1) to give 277 mg (yield 86%) of the title compound.

$^1$H-NMR($CDCl_3$): δ=1.23 (6H, dd, J=1.6, 7.3, $\underline{CH}(CH_3)_2$), 1.28 (3H, d, J=6.8, 4-$CH_3$), 2.56-2.70 (2H, m, $C_6H_5\underline{CH_2}$, $\underline{CH}(CH_3)_2$), 2.86-3.02 (2H, m, H-2, $C_6H_5\underline{CH_2}$), 3.56 (1H, bs, H-8), 3.93 (3H, s, 4'-$OCH_3$), 4.89-4.95 (1H, m, H-4), 5.12 (2H, s, $C_6H_5\underline{CH_2}O$), 5.09-5.40 (3H, m, H-3, 7, 8), 6.82 (1H, d, J=5.4, H-5'), 7.10-7.48 (10H, m, $\underline{C_6H_5}CH_2$, $\underline{C_6H_5}CH_2O$), 8.05 (1H, d, J=5.4, H-6'), 9.00 (1H, d, J=8.4, CONH)

MS (TSP): m/z=621 (M+H)

Example 16

(1)(2R,3R,4S,7S)-7-(3-Benzyloxy-4-methoxy-6-acetoxypicolinylamino)-2-benzyl-5,9-dioxa-3-isobutyryl-oxy-4-methyl-1,6-cyclononanedione; and (2) (2R,3R,4S,7S)-7-(3-Benzyloxy-6-hydroxy-4-methoxypicolinylamino)-2-benzyl-5,9-dioxa-3-isobutyryloxy-4-methyl-1,6-cyclononanedione The compound (277 mg) obtained in Example 15 was dissolved in 25 mL of acetic anhydride. The solution was heated at 80° C. for 2.5 hr. The reaction solution was concentrated. The residue was purified by column chromatography on silica gel (hexane:ethyl acetate=1: 1) and then by column chromatography on silica gel (chloroform:methanol =30 : 1) to give 30 mg (yield 10%) of the title compound (1) and 9 mg (yield 3%) of the title compound (2).

Title compound (1)

$^1$H-NMR ($CDCl_3$): δ=1.23 (6H, dd, J=1.6, 7.3, $CH(\underline{CH_3})_2$), 1.30 (3H, d, J=6.8, 4-$CH_3$), 2.33 (3H, s, 6'-$OCOCH_3$), 2.50-2.72 (2H, m, $C_6H_5\underline{CH_2}$, $\underline{CH}(CH_3)_2$), 2.90-2.99 (2H, m, H-2, $C_6H_5\underline{CH_2}$), 3.55 (1H, bs, H-8), 3.91 (3H, s, 4'-$OCH_3$), 4.90-5.00 (1H, m, H-4), 5.06 (2H, s, $C_6H_5\underline{CH_2}O$), 5.08-5.40 (3H, m, H-3, 7, 8), 7.12 (1H, d, J=5.4, H-5'), 7.13-7.57 (10H, m, $\underline{C_6H_5}CH_2$, $\underline{C_6H_5}CH_2O$), 7.50 (1H, d, J=5.4, H-6'), 8.13 (1H, d, J=8.4, CONH)

MS (TSP): m/z=663 (M+H)

Title compound (2)

$^1$H-NMR ($CDCl_3$): δ=1.18 (6H, dd, J=1.6, 7.3, $CH(CH_3)_2$, 1.25 (3H, d, J=6.8, 4-$CH_3$), 2.50-2.70 (2H, m, $C_6H_5CH_2$, $CH(CH_3)_2$), 2.86-3.02 (2H, m, H-2, $C_6H_5CH_2$, H-8), 3.86 (3H, s, 4'-$OCH_3$), 4.80-5.23 (6H, m, H-3, 4, 7, 8, $C_6H_5CH_2O$), 6.02 (1H, s, H-5), 7.04-7.29 (10H, m, $C_6H_5CH_2$, $C_6H_5CH_2O$), 8.49 (1H, d, J=7.2, CONH)

MS (TSP): m/z=621 (M+H)

Example 17

(2R,3R,4S,7S)-7-(3-Hydroxy-6-methoxypicolinyl-amino)-2-benzyl-5,9-dioxa-3-isobutyryloxy-4-methyl-1,6-cyclononanedione The title compound (16 mg, yield 16%) was obtained in the same manner as in Example 4, except that 3-hydroxy-6-methoxypicolinic acid was used instead of 2-hydroxynicotinic acid.

$^1$H-NMR ($CDCl_3$): δ=1.23 (6H, dd, J=2.5, 6.8, $CH(CH_3)_2$), 1.32 (3H, d, J=6.3, 4-$CH_3$), 2.60-2.75 (2H, m, $C_6H_5CH_2$, $CH(CH_3)_2$), 2.90-3.00 (2H, m, H-2, $C_6H_5CH_2$), 3.62 (1H, bs, H-8), 3.94 (3H, s, 6'-$OCH_3$), 4.97-5.00 (1H, m, H-4), 5.16-5.30 (3H, m, H-3, 7, 8), 6.87 (1H, d, J=5.1, H-5'), 7.12-7.28 (5H, m, $C_6H_5CH_2$), 7.98 (1H, d, J=5.1, H-6'), 8.59 (1H, d, J=8.1, CONH), 11.78 (1H, s, 3'-OH)

MS (FAB): m/z=515 (M+H)

Example 18

(2R,3R,4S,7S)-7-(3-Acetoxy-4-methoxypicolinylamino)-2-benzyl-5,9-dioxa-3-isobutyryloxy-4-methyl-1,6-cyclo-nonanedione UK-2A (6.32 g) was dissolved in 80 mL of pyridine. Acetic anhydride (2.5 mL) was added to the solution under ice cooling, and a reaction was allowed to proceed at room temperature for 3 hr. The reaction solution was concentrated under the reduced pressure to dryness. Thus, 6.7 g (yield 100%) of the title compound was obtained as a white solid.

$^1$H-NMR ($CDCl_3$): δ=1.24 (6H, d, J=6.9, $CH(CH_3)_2$), 1.30 (3H, d, J=6.2, 4-$CH_3$), 2.38 (3H, s, $OCOCH_3$), 2.61 (1H, septet, J=6.9, $CH(CH_3)_2$), 2.70 (1H, d, J=11.4, $C_6H_5CH_2$), 2.87-2.99 (2H, m, H-2, $C_6H_5CH_2$), 3.57 (1H, bs, H-8), 3.90 (3H, s, $OCH_3$), 4.96 (1H, dq, J=9.5, 6.2, H-4), 5.14 (1H, t, J=8.4, H-7), 5.20 (1H, t, J=9.5, H-3), 5.34 (1H, bs, H-8), 7.01 (1H, d, J=5.5, H-5'), 7.11-7.28 (5H, m, $C_6H_5$), 8.32 (1H, d, J=5.5, H-6'), 8.63 (1H, d, CONH, J=8.4)

MS (TSP): m/z=557 (M+H)

Example 19

(2R,3R,4S,7S)-7-(3-Benzoyloxy-4-methoxypicolinylamino)-2-benzyl-5,9-dioxa-3-isobutyryloxy-4-methyl-1,6-cyclo-nonanedione UK-2A (50 mg) was dissolved in 5 mL of pyridine. Benzoyl chloride (27 mg) was added to the solution under ice cooling, and a reaction was allowed to proceed at room temperature for 2 hr. The reaction solution was diluted with methylene chloride. The diluted solution was washed twice with water, dried over magnesium sulfate, and then concentrated under the reduced pressure. The residue was purified by column chromatography on silica gel (ethyl acetate: hexane =3 : 1) to give 33 mg (yield 55%) of the title compound.

$^1$H-NMR ($CDCl_3$): δ=1.22 (6H, d, J=7.1, $CH(CH_3)_2$), 1.27 (3H, d, J=6.0, 4-$CH_3$), 2.50-2.70 (2H, m, $CH(CH_3)_2$, $C_6H_5CH_2$), 2.80-3.00 (2H, m, H-2, $C_6H_5CH_2$), 3.60 (1H, bs, H-8), 3.89 (3H, S, $OCH_3$), 4.90-5.30 (4H, m, H-3, 4, 7, 8), 7.06 (1H, d, J=5.5, H-5'), 7.09-7.26 (5H, m, $CH_2C_6H_5$), 7.48-7.66, 8.20-8.23 (3H, 2H, m, $COC_6H_5$), 8.38 (1H, d, J=5.5, H-6'), 8.66 (1H, d, J=8.2, CONH)

MS (TSP): m/z=619 (M+H)

Example 20

(2R,3R,4S,7S)-7-(3-Isopropyloxycarbonyloxy-4-methoxy-picolinylamino)-2-benzyl-5,9-dioxa-3-isobutyryloxy-4-methyl-1,6-cyclononanedione UK-2A (50 mg) was dissolved in 5 mL of methylene chloride. Triethylamine (1 mL) and 1 mL of isopropyl chloroformate were added to the solution under ice cooling, and a reaction was allowed to proceed at room temperature for one hr. The reaction solution was diluted with methylene chloride. The diluted solution was washed twice with water, dried over magnesium sulfate, and then concentrated under the reduced pressure to give 58 mg (yield 100%) of the title compound.

$^1$H-NMR ($CDCl_3$): δ=1.20-1.40 (15H, m, $OCOCH(CH_3)_2$, $OCH(CH_3)_2$, 4-$CH_3$), 2.50-2.80 (2H, m, $CH(CH_3)_2$, $C_6H_5CH_2$), 2.80-3.10 (2H, m, H-2, $C_6H_5CH_2$), 3.60 (1H, bs, H-8), 3.92 (3H, s, $OCH_3$), 4.93-5.40 (5H, m, $OCH(CH_3)_2$, H-3, 4, 7, 8), 7.02 (1H, d, J=5.5, H-5'), 7.11-7.29 (5H, m, $C_6H_5$), 8.33 (1H, d, J=5.5, H-6'), 8.58 (1H, d, J=8.2,CONH)

MS (TSP): m/z=601 (M+H)

Example 21

(2R,3R,4S,7S)-7-(3-(3-Methoxycarbonylpropionyloxy)-4-methoxypicolinylamino)-2-benzyl-5,9-dioxa-3-isobutyryl-oxy-4-methyl-1,6-cyclononanedione A solution of 100 mg of UK-2A and 0.27 mL of triethylamine in methylene chloride (20 mL) was added dropwise to a mixture of 0.22 mL of succinic acid chloride with 5 mL of methylene chloride under ice cooling, and a reaction was allowed to proceed at room temperature for 2 hr. The reaction solution was again cooled with ice. Methanol (10 mL) was added thereto, and a reaction was allowed to proceed at room temperature for one hr. The reaction solution was diluted with methylenechloride. The diluted solution was washed twice with water, dried over magnesium sulfate, and then concentrated under the reduced pressure. The residue was purified by column chromatography on silica gel (ethyl acetate:hexane =1: 1) to give 53 mg (yield 44%) of the title compound.

$^1$H-NMR ($CDCl_3$): δ=1.23 (6H, d, J=7.1, $CH(CH_3)_2$), 1.31 (3H, d, J=6.0, 4-$CH_3$), 2.50-3.10 (8H, m, $CH(CH_3)_2$, $COCH_2CH_2CO$, $C_6H_5CH_2$, H-2), 3.72 (3H, s, $COOCH_3$), 3.90 (3H, s, $OCH_3$), 4.90-5.40 (4H, m, H-3, 4, 7, 8), 7.00 (1H, d, J=5.4, H-5'), 7.11-7.28 (5H, m, $C_6H_5$), 8.32 (1H, d, J=5.4, H-6'), 8.62 (1H, d, J=8.4, CONH)

MS (FAB): m/z=629 (M+H)

Example 22

(2R,3R,4S,7S)-7-(3-(3-Benzyloxycarbonylpropionyloxy)-4-methoxypicolinylamino)-2-benzyl-5,9-dioxa-3-isobutyryl-oxy-4-methyl-1,6-cyclononanedione UK-2A (100 mg), 49 mg of monobenzyl succinate, and 55 mg of 4-dimethylamino pyridine were dissolved in 20 mL of methylene chloride. Dicyclohexylcarbodiimide (60 mg) was added to the solution under ice cooling, and a reaction was allowed to proceed at room temperature for 6 hr. The precipitate was removed by filtration. The filtrate was washed with 1 N hydrochloric acid, saturated aqueous sodium hydrogencarbonate, and water in that order, dried over magnesium sulfate, and then concentrated under the reduced pressure. The residue was purified by column chromatography on silica gel (ethyl acetate:hexane =1: 1) to give 92 mg (yield 69%) of the title compound.

$^1$H-NMR ($CDCl_3$): δ=1.24 (6H, d, J=7.1, $CH\underline{(CH_3)_2}$), 1.30 (3H, d, J=6.0, 4-$CH_3$), 2.58-3.07 (8H, m, $\underline{CH}(CH_3)_2$, $CO\underline{CH_2CH_2}CO$, $C_6H_5\underline{CH_2}$, H-2), 3.55 (1H, bs, H-8), 3.86 (3H, s, $OCH_3$), 5.16 (2H, s, $COO\underline{CH_2}C_6H_5$), 4.90-5.40 (4H, m, H-3, 4, 7, 8), 6.99 (1H, d, J=5.4, H-5'), 7.11-7.37 (10H, m, $C_6H_5$×2), 8.31 (1H, d, J=5.4, H-6'), 8.61 (1H, d, J=8.4, CONH)

MS (FAB): m/z=705 (M+H)

Example 23

(2R,3R,4S,7S)-7-(3-(4-Methoxycarbonylbutyryloxy)-4-methoxypicolinylamino)-2-benzyl-5,9-dioxa-3-isobutyryl-oxy-4-methyl-1,6-cyclononanedione The title compound (yield 20%) was obtained in the same manner as in Example 21, except that glutaric acid chloride was used instead of succinic acid chloride.

$^1$H-NMR($CDCl_3$): δ=1.23 (6H, dd, J=1.6, 7.3, $CH\underline{(CH_3)_2}$), 1.29 (3H, d, J=6.8, 4-$CH_3$), 2.09 (2H, q, J=7.3, $CH_2\underline{CH_2}CH_2$), 2.50, 2.75 (each 2H, each t, each J=7.3, $\underline{CH_2}CH_2\underline{CH_2}$), 2.58-2.70 (2H, m, $\underline{CH}(CH_3)_2$, $C_6H_5\underline{CH_2}$), 2.90-3.00 (2H, m, $C_6H_5\underline{CH_2}$, H-2), 3.60 (1H, bs, H-8), 3.69 (3H, s, $COOCH_3$), 3.89 (3H, s, 4'-$OCH_3$), 4.90-5.00 (1H, m, H-4), 5.10-5.40 (3H, m, H-3, 7, 8), 7.00 (1H, d, J=5.4, H-5'), 7.10-7.28 (5H, m, $C_6H_5$), 8.32 (1H, d, J=5.4, H-6'), 8.61 (1H, d, J=8.4, CONH)

MS (ESI): m/z=643 (M+H)

Example 24

(2R,3R,4S,7S)-7-(3-(5-Methoxycarbonylvaleryloxy)-4-methoxypicolinylamino)-2-benzyl-5,9-dioxa-3-isobutyryl-oxy-4-methyl-1,6-cyclononanedione The title compound (yield 57%) was obtained in the same manner as in Example 21, except that adipic acid chloride was used instead of succinic acid chloride.

$^1$H-NMR($CDCl_3$):δ=1.23 (6H, dd, J=1.6, 7.3, $CH\underline{(CH_3)_2}$), 1.30 (3H, d, J=6.8, 4-$CH_3$), 1.59-1.67, 1.78-1.86 (each 2H, each m, $CH_2\underline{CH_2CH_2}CH_2$), 2.23-2.48 (4H, m, $\underline{CH_2}CH_2CH_2\underline{CH_2}$), 2.56-2.99 (4H, m, H-2, $\underline{CH}(CH_3)_2$, $C_6H_5\underline{CH_2}$), 3.55 (1H, bs, H-8), 3.62 (3H, s, $COOCH_3$), 3.88 (3H, s, 4'-$OCH_3$), 4.93-4.99 (1H, m, H-4), 5.16-5.32 (3H, m, H-3, 7, 8), 6.99 (1H, d, J=5.4, H-5'), 7.10-7.28 (5H, m, $C_6H_5$), 8.30 (1H, d, J=5.4, H-6'), 8.59 (1H, d, J=8.4, CONH)

MS (ESI): m/z=657 (M+H)

Example 25

(2R,3R,4S,7S)-7-(3-(6-Methoxycarbonylhexanoyloxy)-4-methoxypicolinylamino)-2-benzyl-5,9-dioxa-3-isobutyryl-oxy-4-methyl-1,6-cyclononanedione The title compound (yield 85%) was obtained in the same manner as in Example 21, except that pimelic acid chloride was used instead of succinic acid chloride.

$^1$H-NMR ($CDCl_3$): δ=1.23 (6H, dd, J=1.6, 7.3, $CH\underline{(CH_3)_2}$), 1.30 (3H, d, J=6.8, 4-$CH_3$), 1.35-1.84 (6H, m, $CH_2\underline{(CH_2)_3}CH_2$), 2.29-2.38 (4H, m, $\underline{CH_2}(CH_2)_3\underline{CH_2}$), 2.58-2.70 (2H, m, $\underline{CH}(CH_3)_2$, $C_6H_5\underline{CH_2}$), 2.90-3.00 (2H, m, $C_6H_5\underline{CH_2}$, H-2), 3.55 (1H, bs, H-8), 3.67 (3H, s, $COOCH_3$), 3.89 (3H, s, 4'-$OCH_3$), 4.90-5.10 (1H, m, H-4), 5.10-5.30 (3H, m, H-3, 7, 8), 7.00 (1H, d, J=5.4, H-5'), 7.10-7.28 (5H, m, $C_6H_5$), 8.32 (1H, d, J=5.4, H-6'), 8.62 (1H, d, J=8.4, CONH)

MS (ESI): m/z=671 (M+H)

Example 26

(2R,3R,4S,7S)-7-(3-(8-Methoxycarbonyloctanoyloxy)-4-methoxypicolinylamino)-2-benzyl-5,9-dioxa-3-isobutyryl-oxy-4-methyl-1,6-cyclononanedione The title compound (yield 24%) was obtained in the same manner as in Example 21, except that azelaic acid chloride was used instead of succinic acid chloride.

$^1$H-NMR ($CDCl_3$): δ=1.23 (6H, dd, J=1.6, 7.3, $CH\underline{(CH_3)_2}$), 1.30 (3H, d, J=6.8, 4-$CH_3$), 1.30-1.90 (10H, m, $CH_2\underline{(CH_2)_5}CH_2$), 2.27-2.37 (4H, m, $\underline{CH_2}(CH_2)_5\underline{CH_2}$), 2.50-2.80 (2H, m, $\underline{CH}(CH_3)_2$, $C_6H_5\underline{CH_2}$), 2.80-3.10 (2H, m, $C_6H_5\underline{CH_2}$, H-2), 3.55 (1H, bs, H-8), 3.66 (3H, s, $COOCH_3$), 3.89 (3H, s, 4'-$OCH_3$), 4.90-5.00 (1H, m, H-4), 5.10-5.40 (3H, m, H-3, 7, 8), 7.00.(1H, d, J=5.4, H-5'), 7.10-7.26 (5H, m, $C_6H_5$), 8.31 (1H, d, J=5.4, H-6'), 8.61 (1H, d, J=8.4, CONH)

MS (ESI): m/z=699 (M+H)

Example 27

(2R,3R,4S,7S)-7-(3-(9-Methoxycarbonylnonanoyloxy)-4-methoxypicolinylamino)-2-benzyl-5,9-dioxa-3-isobutyryl-oxy-4-methyl-1,6-cyclononanedione The title compound (yield 45%) was obtained in the same manner as in Example 21, except that sebacic acid chloride was used instead of succinic acid chloride.

$^1$H-NMR ($CDCl_3$): δ=1.23 (6H, dd, J=1.6, 7.3, $CH\underline{(CH_3)_2}$), 1.30 (3H, d, J=6.8, 4-$CH_3$), 1.31-1.80 (12H, m, $CH_2\underline{(CH_2)_6}CH_2$), 2.28-2.33 (4H, m, $\underline{CH_2}(CH_2)_6\underline{CH_2}$), 2.50-2.70 (2H, m, $CH(CH_3)_2$, $C_6H_5\underline{CH_2}$), 2.90-3.00 (2H, m, $C_6H_5\underline{CH_2}$, H-2), 3.55 (1H, bs, H-8), 3.66 (3H, s, $COOCH_3$), 3.89 (3H, s, 4'-$OCH_3$), 4.90-5.00 (1H, m, H-4), 5.10-5.40 (3H, m, H-3, 7, 8), 6.99 (1H, d, J=5.4, H-5'), 7.10-7.28 (5H, m, $C_6H_5$), 8.31 (1H, d, J=5.4, H-6'), 8.62 (1H, d, J=8.4, CONH)

MS (ESI): m/z=713 (M+H)

Example 28

(2R,3R,4S,7S)-7-(3-(4-Benzyloxycarbonylbutyryloxy)-4-methoxypicolinylamino)-2-benzyl-5,9-dioxa-3-isobutyryl-oxy-4-methyl-1,6-cyclononanedione A methylene chloride solution (2 mL) containing 0.052 mL of benzyl alcohol and 0.083 mL of triethylamine was added dropwise to 6 mL of a methylene chloride solution containing 0.064 mL of glutaric acid chloride under ice cooling. The mixture was stirred at the same temperature for 30 min. A methylene chloride solution (2 mL) containing 100 mg of UK-2A and 0.14 mL of triethylamine was added dropwise thereto, and a reaction was allowed to proceed under ice cooling for 3 hr. Water was added to the reaction solution, followed by separation. The organic layer was dried over magnesium sulfate, and concentrated under the reduced pressure. The residue was purified by column chromatography on silica gel (ethyl acetate:hexane =1 : 1) to give 122 mg (yield 89%) of the title compound.

$^1$H-NMR ($CDCl_3$): δ=1.24 (6H, dd, J=1.6, 7.3, $CH(CH_3)_2$), 1.29 (3H, d, J=6.8, 4-$CH_3$), 2.11 (2H, q, J=7.3, $CH_2CH_2CH_2$), 2.40-2.70 (2H, m, $C_6H_5CH_2$, $CH(CH_3)_2$), 2.55, 2.75 (each 2H, each t, each J=7.3, $CH_2CH_2CH_2$), 2.80-3.10 (2H, m, H-2, $C_6H_5CH_2$), 3.55 (1H, bs, H-8), 3.86 (3H, s, 4'-$OCH_3$), 4.90-5.00 (1H, m, H-4), 5.14 (2H, s, $C_6H_5CH_2O$), 5.10-5.35 (3H, m, H-3, 7, 8), 6.99 (1H, d, J=5.4, H-5'), 7.10-7.37 (10H, m, $C_6H_5CH_2$, $C_6H_5CH_2O$), 8.31 (1H, d, J=5.4, H-6'), 8.60 (1H, d, J=8.4, CONH)

MS (FAB): m/z=719 (M+H)

Example 29

(2R,3R,4S,7S)-7-(3-(5-Benzyloxycarbonylvaleryloxy)-4-methoxypicolinylamino)-2-benzyl-5,9-dioxa-3-isobutyryl-oxy-4-methyl-1,6-cyclononanedione The title compound (yield 25%) was obtained in the same manner as in Example 28, except that adipic acid chloride was used instead of glutaric acid chloride.

$^1$H-NMR ($CDCl_3$): δ=1.23 (6H, dd, J=1.6, 7.3, $CH(CH_3)_2$), 1.29 (3H, d, J=6.8, 4-$CH_3$), 1.70-1.80 (4H, m, $CH_2(CH_2)_2CH_2$), 2.30-2.50 (4H, m, $CH_2(CH_2)_2CH_2$), 2.60-2.70 (2H, m, $C_6H_5CH_2$, $CH(CH_3)_2$), 2.80-3.00 (2H, m, H-2, $C_6H_5CH_2$), 3.55 (1H, bs, H-8), 3.85 (3H, s, 4'-$OCH_3$), 4.90-5.00 (1H, m, H-4), 5.12 (2H, s, $C_6H_5CH_2O$), 5.10-5.40 (3H, m, H-3, 7, 8), 6.98 (1H, d, J=5.4, H-5'), 7.10-7.35 (10H, m, $C_6H_5CH_2$, $C_6H_5CH_2O$), 8.31 (1H, d, J=5.4, H-6'), 8.60 (1H, d, J=8.4, CONH)

MS (FAB): m/z=(M+H)

Example 30

(2R,3R,4S,7S)-7-(3-(6-Benzyloxycarbonylhexanoyloxy)-4-methoxypicolinylamino)-2-benzyl-5,9-dioxa-3-isobutyryl-oxy-4-methyl-1,6-cyclononanedione The title compound (yield 62%) was obtained in the same manner as in Example 28, except that pimelic acid chloride was used instead of glutaric acid chloride.

$^1$H-NMR ($CDCl_3$): δ=1.23 (6H, dd, J=1.6, 7.3, $CH(CH_3)_2$), 1.29 (3H, d, J=6.8, 4-$CH_3$), 1.37-1.86 (6H, m, $CH_2(CH_2)_3CH_2$), 2.31-2.45 (4H, m, ($CH_2(CH_2)_3CH_2$), 2.58-2.71 (2H, m, $C_6H_5CH_2$, $CH(CH_3)_2$), 2.91-2.99 (2H, m, H-2, $C_6H_5CH_2$), 3.55 (1H, bs, H-8), 3.87 (3H, s, 4'-$OCH_3$), 4.90-5.00 (1H, m, H-4), 5.11 (2H, s, $C_6H_5CH_2O$), 5.11-5.40 (3H, m, H-3, 7, 8), 6.99 (1H, d, J=5.4, H-5'), 7.10-7.36 (10H, m, $C_6H_5CH_2$, $C_6H_5CH_2O$), 8.31 (1H, d, J=5.4, H-6'), 8.61 (1H, d, J=8.4, CONH)

MS (FAB): m/z=747 (M+H)

Example 31

(2R,3R,4S,7S)-7-(3-(9-Benzyloxycarbonylnonanoyloxy)-4-methoxypicolinylamino)-2-benzyl-5,9-dioxa-3-isobutyryl-oxy-4-methyl-1,6-cyclononanedione The title compound (yield 53%) was obtained in the same manner as in Example 28, except that sebacic acid chloride was used instead of glutaric acid chloride.

$^1$H-NMR ($CDCl_3$): δ=1.23 (6H, dd, J=1.6, 7.3, $CH(CH_3)_2$), 1.29 (3H, d, J=6.8, 4-$CH_3$), 1.30-1.90 (12H, m, $CH_2(CH_2)_6CH_2$), 2.30-2.38 (4H, m, $CH_2(CH_2)_6CH_2$), 2.61-2.68 (2H, m, $C_6H_5CH_2$, $CH(CH_3)_2$), 2.90-3.05 (2H, m, H-2, $C_6H_5CH_2$), 3.55 (1H, bs, H-8), 3.88 (3H, s, 4'-$OCH_3$), 4.90-5.00 (1H, m, H-4), 5.11 (2H, s, $C_6H_5CH_2O$), 5.11-5.35 (3H, m, H-3, 7, 8, ), 6.99 (1H, d, J=5.4, H-5'), 7.10-7.36 (10H, m, $C_6H_5CH_2$, $C_6H_5CH_2O$), 8.31 (1H, d, J=5.4, H-6'), 8.60 (1H, d, J=8.4, CONH)

MS (FAB): m/z=789 (M+H)

Example 32

(2R,3R,4S,7S)-7-(3-(4-Butyloxycarbonylbutyryloxy)-4-methoxypicolinylamino)-2-benzyl-5,9-dioxa-3-isobutyryl-oxy-4-methyl-1,6-cyclononanedione The title compound (yield 53%) was obtained in the same manner as in Example 28, except that n-butanol was used instead of benzyl alcohol.

$^1$H-NMR ($CDCl_3$): δ=1.23 (6H, dd, J=1.6, 7.3, $CH(CH_3)_2$), 1.33 (3H, d, J=6.8, 4-$CH_3$), 1.37-1.46, 1.57-1.65, 2.04-2.11 (9H, m, $COCH_2CH_2CH_2CO$, $OCH_2$, $OCH_2(CH_2)_2CH_3$), 2.37-2.51 (4H, m, $COCH_2CH_2CH_2CO$), 2.58-2.77 (2H, m, $COCH_2CH_2CH_2CO$, $CH(CH_3)_2$, $C_6H_5CH_2$), 3.55 (1H, bs, H-8), 3.89 (3H, s, 4'-$OCH_3$), 4.90-5.00 (1H, m, H-4), 5.00-5.40 (3H, m, H-3, 7, 8), 7.00 (1H, d, J=5.4, H-5'), 7.10-7.28 (5H, m, $C_6H_5CH_2$), 8.32 (1H, d, J=5.4, H-6'), 8.63 (1H, d, J=8.4, CONH)

MS (FAB): m/z=685 (M+H)

Example 33

(2R,3R,4S,7S)-7-(3-(6-Carboxyhexanoyloxy)-4-methoxy-picolinylamino)-2-benzyl-5,9-dioxa-3-isobutyryloxy-4-methyl-1,6-cyclononanedione The compound (77 mg) obtained in Example 30 was dissolved in 40 mL of methanol. 10% palladium-carbon (8 mg) was added to the solution, followed by catalytic hydrogenation at room temperature under normal pressure. Two hr after the initiation of the reaction, the catalyst was removed by filtration. The filtrate was concentrated to dryness. The residue was purified by chromatography on silica gel (chloroform:methanol =30 : 1) to give 44.8 mg (yield 66%) of the title compound.

$^1$H-NMR ($CDCl_3$): δ=1.23 (6H, dd, J=1.6, 7.3, $CH(CH_3)_2$), 1.29 (3H, d, J=6.8, 4-$CH_3$), 1.40-1.80 (6H, m, $CH_2(CH_2)_3CH_2$), 2.20-2.40 (4H, m, $CH_2(CH_2)_3CH_2$), 2.50-2.70

(2H, m, $C_6H_5\underline{CH_2}$, $\underline{CH}(CH_3)_2$), 2.90-3.00 (2H, m, H-2, $C_6H_5C_2$), 3.55 (1H, bs, H-8), 3.88 (3H, s, 4'-$OCH_3$), 4.90-5.00 (1H, m, H-4), 5.10-5.40 (3H, m, H-3, 7, 8), 7.00 (1H, d, J=5.4, H-5'), 7.10-7.26 (5H, m, $\underline{C_6H_5}CH_2$), 8.30 (1H, d, J=5.4, H-6'), 8.62 (1H, d, J=8.4, CONH)

MS (FAB): m/z=657 (M+H)

Example 34

(2R,3R,4S,7S)-7-(3-(9-Carboxynonanoyloxy)-4-methoxy-picolinylamino)-2-benzyl-5,9-dioxa-3-isobutyryloxy-4-methyl-1,6-cyclononanedione The title compound (yield 59%) was obtained in the same manner as in Example 33, except that the compound obtained in Example 31 was used instead of the compound obtained in Example 30.

$^1$H-NMR ($CDCl_3$): δ=1.23 (6H, dd, J=1.6, 7.3, $CH(\underline{CH_3})_2$), 1.29 (3H, d, J=6.8, 4-$CH_3$), 1.31-1.76 (12H, m, $CH_2\underline{(CH_2)_6}CH_2$), 2.30-2.40 (4H, m, $\underline{CH_2}(CH_2)_6\underline{CH_2}$ ), 2.50-2.71 (2H, m, $C_6H_5\underline{CH_2}$, $\underline{CH}(CH_3)_2$), 2.90-3.00 (2H, m, H-2, $C_6H_5\underline{CH_2}$), 3.57 (1H, bs, H-8), 3.88 (3H, s, 4'-$OCH_3$), 4.90-5.00 (1H, m, H-4), 5.10-5.23 (3H, m, H-3, 7, 8), 6.99 (1H, d, J=5.4, H-5'), 7.10-7.34 (5H, m, $\underline{C_6H_5}CH_2$), 8.31 (1H, d, J=5.4, H-6'), 8.62 (1H, d, J=8.4, CONH)

MS (FAB): m/z=699 (M+H)

Example 35

(2R,3R,4S,7S)-7-(3-(N-Carbobenzyloxy-L-alanyl)oxy-4-methoxypicolinylamino)-2-benzyl-5,9-dioxa-3-isobutyryl-oxy-4-methyl-1,6-cyclononanedione UK-2A (200 mg), 170 mg of N-carbobenzyloxy-L-alanine and 186 mg of dimethylaminopyridine were dissolved in 10 mL of methylene chloride. 1-Ethyl-3-(3-dimethylaminopropyl)-carbodiimide hydrochloride (218 mg) was added to the solution, and a reaction was allowed to proceed at room temperature for 4 hr. Dichloromethane and 1 N hydrochloric acid were added to the reaction solution, followed by separation. The organic layer was dried over magnesium sulfate, and then concentrated under the reduced pressure. The residue was purified by chromatography on silica gel (chloroform:methanol =100 : 1) to give 143 mg (yield 52%) of the title compound.

$^1$H-NMR ($CDCl_3$): δ=1.23 (6H, dd, J=1.6, 7.3, $CH(\underline{CH_3})_2$), 1.33 (3H, d, J=6.8, 4-$CH_3$), 1.62 (3H, d, $CH_3$ (alanyl)), 2.59-2.72 (2H, m, $C_6H_5CH_2$, $\underline{CH}(CH_3)_2$), 2.92-3.00 (2H, m, H-2, $C_6H_5\underline{CH_2}$), 3.55 (1H, bs, H-8), 3.87 (3H, s, 4'-$OCH_3$), 4.90-5.00 (1H, m, H-4), 5.10-5.40 (5H, m, H-3, 7, 8, $C_6H_5\underline{CH_2}O$), 5.70 (1H, bs, CONH(alanyl)), 7.00 (1H, d, J=5.4, H-5), 7.11-7.36 (10H, m, $\underline{C_6H_5}CH_2$, $\underline{C_6H_5}CH_2O$), 8.32 (1H, d, J=5.4, H-6'), 8.63 (1H, m, J=8.4, CONH)

MS (TSP): m/z=720 (M+H)

Example 36

(2R,3R,4S,7S)-7-(3-Diphenyphosphoryloxy-4-methoxy-picolinylamino)-2-benzyl-5,9-dioxa-3-isobutyryloxy-4-methyl-1,6-cyclononanedione UK-2A (100 mg) and 36 mg of 4-dimethylaminopyridine were dissolved in 3 mL of methylene chloride. Pyridine (24 μl) and 79 mg of diphenyl chlorophosphite were added to the solution under ice cooling, and a reaction was allowed to proceed at room temperature for 2 hr. The reaction solution was diluted with methylene chloride. The diluted solution was washed with 1 N hydrochloric acid and water in that order. The organic layer was dried over magnesium sulfate, and then concentrated under the reduced pressure. The residue was purified by chromatography on silica gel (ethyl acetate:hexane=2 :1) to give 140 mg (yield 99%) of the title compound.

$^1$H-NMR ($CDCl_3$): δ=1.27 (6H, dd, J=1.6, 7.3, $CH(\underline{CH_3})_2$), 1.32 (3H, d, J=6.8, 4-$CH_3$), 2.60-2.80 (2H, m, $C_6H_5\underline{CH_2}$, $\underline{CH}(CH_3)_2$), 2.90-3.10 (2H, m, H-2, $C_6H_5\underline{CH_2}$), 3.55 (1H, bs, H-8), 3.67 (3H, s, 4'-$OCH_3$), 4.90-5.00 (1H, m, H-4), 5.10-5.32 (3H, m, H-3, 7, 8), 6.98 (1H, d, J=5.4, H-5'), 7.15-7.36 (15H, m, $\underline{C_6H_5}CH_2$, $(C_6H_5O)_2PO$), 8.31 (1H, d, J=5.4, H-6'), 8.41 (1H, d, J=8.4, CONH)

MS (TSP): m/z=605 (M+H)

Example 37

(2R,3R,4S,7S)-7-(3-Diethxyphosphoryloxy)-4-methoxy-picolinylamino)-2-benzyl-5,9-dioxa-3-isobutyryloxy-4-methyl-1,6-cyclononanedione The title compound (yield 43%) was obtained in the same manner as in Example 36, except that diethyl chlorophosphite was used instead of diphenyl chlorophosphite.

$^1$H-NMR($CDCl_3$): δ=1.23 (6H, dd, J=1.6, 7.3, $CH(\underline{CH_3})_2$), 1.30 (3H, d, J=6.8, 4-$CH_3$), 1.33-1.40 (6H, m, $(OCH_2\underline{CH_3})_2$), 2.59-2.72 (2H, m, $C_6H_5CH_2$, $\underline{CH}(CH_3)_2$), 2.90-3.00 (2H, m, H-2, $C_6H_5\underline{CH_2}$), 3.60 (1H, bs, H-8), 3.93 (3H, s, 4'-$OCH_3$), 4.23-4.38 (4H, m, $(O\underline{CH_2}CH_2CH_3)_2$), 4.90-5.00 (1H, m, H-4), 5.10-5.40 (3H, m, H-3, 7, 8), 6.98 (1H, d, J=5.4, H-5'), 7.11-7.28 (5H, m, $\underline{C_6H_5}CH_2$), 8.25 (1H, d, J=5.4, H-6'), 8.38 (1H, d, J=8.4, CONH)

MS (TSP): m/z=651 (M+H)

Example 38

(2R,3R,4S,7S)-7-(3-Methoxysalicylamino)-2-benzyl-5,9-dioxa-3-isobutyryloxy-4-methyl-1,6-cyclononanedione The title compound (yield 74%) was obtained in the same manner as in Example 4, except that 3-methoxysalicylic acid was used instead of 2-hydroxynicotinic acid.

$^1$H-NMR ($CDCl_3$): δ=1.24 (6H, d, J=7.3, $CH(\underline{CH_3})_2$), 1.33 (3H, d, J=6.5, 4-$CH_3$), 2.60-2.73 (2H, m, $\underline{CH}(CH_3)_2$, $C_6H_5\underline{CH_2}$), 2.92-3.05 (2H, m, H-2, $C_6H_5\underline{CH_2}$), 3.63 (1H, bs, H-8), 3.90 (3H, s, $OCH_3$), 4.90-5.26 (3H, m, H-3, 4, 7), 5.18-5.25 (2H, m, H-3, H-7), 5.45 (1H, bs, H-8), 6.81-7.29 (8H, m, aromatic), 7.46 (1H, d, J=6.5, CONH), 10.75 (1H, s, OH)

MS (TSP): m/z=514 (M+H)

Example 39

(2R,3R,4S,7S)-7-Salicylamino-2-benzyl-5,9-dioxa-3-isobutyryloxy-4-methyl-1,6-cyclononanedione The title compound (yield 42%) was obtained in the same manner as in Example 4, except that salicylic acid was used instead of 2-hydroxynicotinic acid.

$^1$H-NMR ($CDCl_3$): δ=1.20-1.36 (9H, m, $CH(\underline{CH_3})_2$, 4-$CH_3$), 2.60-2.80 (2H, m, $\underline{CH}(CH_3)_2$, $C_6H_5\underline{CH_2}$), 2.91-3.00 (2H, m, $C_6H_5\underline{CH_2}$, H-2), 3.60 (1H, bs, H-8), 4.98-5.27 (3H, m, H-3, 4, 7), 5.45 (1H, bs, H-8), 6.84-7.44 (10H, m, aromatic, CONH), 11.80 (1H, s, OH)

MS (TPS): m/z=484 (M+H)

Example 40

(2R,3R,4S,7S)-7-(3-Nitrosalicyl)amino-2-benzyl-5,9-dioxa-3-isobutyryloxy-4-methyl-1,6-cyclononanedione The title compound (yield 66%) was obtained in the same manner as in Example 4, except that 3-nitrosalicylic acid was used instead of 2-hydroxynicotinic acid.

$^1$H-NMR ($CDCl_3$)δ: 1.23-1.37 (9H, m, $\underline{CH(CH_3)_2}$, 4-$CH_3$), 2.60-2.80 (2H, m, $\underline{CH}(CH_3)_2$, $C_6H_5\underline{CH_2}$), 2.80-3.10 (2H, m, $C_6H_5\underline{CH_2}$, H-2), 3.60 (1H, bs, H-8), 4.98 (1H, bs, H-4), 5.18-5.30 (2H, m, H-3, 7), 5.42 (1H, bs, H-8), 7.06-7.29 (6H, m, $C_6H_5$, H-6'), 8.27 (1H, d, J=7.6, H-5'), 8.45 (1H, d, J=7.6, H-4'), 8.76 (1H, bs, CONH)

MS (TPS): m/z=527 (M−H)

Example 41

(2R,3R,4S,7S)-7-(3-Aminosalicyl)amino-2-benzyl-5,9-dioxa-3-isobutyryloxy-4-methyl-1,6-cyclononanedione The compound (50 mg) obtained in Example 40 was dissolved in 25 mL of methanol. 10% palladium-carbon (5 mg) was added to the solution, followed by hydrogenation at room temperature under normal pressure for one hr. The catalyst was then removed by filtration. The filtrate was concentrated under the reduced pressure. The residue was purified by column chromatography on silica gel (ethyl acetate:hexane =1 : 1) to give 16 mg (yield 34%) of the title compound.

$^1$H-NMR ($CDCl_3$): δ=1.23 (6H, d, J=7.3, $CH\underline{(CH_3)_2}$), 1.33 (3H, d, J=5.9, 4-$CH_3$), 2.60-2.80 (2H, m, $\underline{CH}(CH_3)_2$, $C_6H_5\underline{CH_2}$), 2.92-3.00 (2H, m, $C_6H_5\underline{CH_2}$, H-2), 3.60 (1H, bs, H-8), 4.00 (2H, bs, $NH_2$), 4.98 (1H, bs, H-4), 5.00-5.50 (2H, m, H-3, 4, 7, 8), 5.42 (1H, bs, H-8), 6.66-7.29 (9H, m, aromatic, CONH), 12.00 (1H, s, OH)

MS (TSP): m/z=499 (M+H)

Example 42

(2R,3R,4S,7S)-7-(3-Formylaminosalicyl)amino-2-benzyl-5,9-dioxa-3-isobutyryloxy-4-methyl-1,6-cyclononanedione The compound (8.8 mg) obtained in Example 41 was dissolved in 1 mL of methylene chloride. Formic acid (0.5 mL) and 0.1 mL of acetic anhydride were added sequentially, and a reaction was allowed to proceed at room temperature for 30 min. Methylenechloride and water were added thereto, followed by separation. The organic layer was dried over magnesium sulfate, and then concentrated under the reduced pressure. The residue was purified by column chromatography on silica gel (ethyl acetate:hexane =1:1) to give 4.2 mg (yield 44%) of the title compound.

$^1$H-NMR ($CDCl_3$): δ=1.20-1.40 (9H, m, $CH(\underline{CH_3})_2$, 4-$CH_3$), 2.60-2.80 (2H, m, $\underline{CH}(CH_3)_2$, $\underline{CH_2}C_6H_5$), 2.80-3.10 (2H, m, $\underline{CH_2}C_6H_5$, H-2), 3.59 (1H, bs, H-8), 5.00-5.26 (4H, m, H-3, 4, 7, 8), 6.66-7.29 (8H, m, aromatic), 12.00 (1H, s, OH)

MS (TSP): m/z=527 (M+H)

Example 43

(2R,3R,4S,7S)-7-(5-Nitrosalicyl)amino-2-benzyl-5,9-dioxa-3-isobutyryloxy-4-methyl-1,6-cyclononanedione The title compound (yield 84%) was obtained in the same manner as in Example 4, except that 5-nitrosalicylic acid was used instead of 2-hydroxynicotinic acid.

$^1$H-NMR ($CDCl_3$): δ=1.22-1.43 (9H, m, $CH\underline{(CH_3)_2}$, 4-$CH_3$), 2.61-2.75 (2H, m, $\underline{CH}(CH_3)_2$, $C_6H_5\underline{CH_2}$), 2.90-3.01 (2H, m, $C_6H_5\underline{CH_2}$, H-2), 3.68 (1H, bs, H-8), 4.90-5.40 (4H, m, H-3, 4, 7, 8), 7.00-7.30 (6H, m, H-3'), 7.58 (1H, d, J=6.5, CONH), 8.27 (1H, dd, J=8.9, 2.2, H-4'), 8.46 (1H, d, J=2.2, H-6')

MS (TSP): m/z=527 (M−H)

Example 44

(2R,3R,4S,7S)-7-(5-Aminosalicyl)amino-2-benzyl-5,9-dioxa-3-isobutyryloxy-4-methyl-1,6-cyclononanedione The title compound (yield 49%) was obtained in the same manner as in Example 41, except that the compound obtained in Example 43 was used instead of the compound obtained in Example 40.

$^1$H-NMR ($CDCl_3$): δ=1.20-1.40 (9H, m, $CH\underline{(CH_3)_2}$, 4-$CH_3$), 2.58-2.80 (2H, m, $\underline{CH}(CH_3)_2$, $C_6H_5\underline{CH_2}$), 2.88-3.04 (2H, m, $C_6H_5\underline{CH_2}$, H-2), 3.58 (1H, bs, H-8), 4.90-5.40 (4H, m, H-3, 4, 7, 8), 6.70-7.30 (9H, m, aromatic, CONH)

MS (TSP): m/z=499 (M+H)

Example 45

(2R,3R,4S,7S)-7-(4-Chlorosalicyl)amino-2-benzyl-5,9-dioxa-3-isobutyryloxy-4-methyl-1,6-cyclononanedione The title compound (yield 26%) was obtained in the same manner as in Example 4, except that 4-chlorosalicylic acid was used instead of 2-hydroxynicotinic acid.

$^1$H-NMR ($CDCl_3$): δ=1.23 (6H, d, J=7.0, $CH\underline{(CH_3)_2}$), 1.34 (3H, d, J=6.5, 4-$CH_3$), 2.40-3.00 (4H, m, $\underline{CH}(CH_3)_2$, $C_6H_5\underline{CH_2}$, H-2), 3.60 (1H, bs, H-8), 4.90-5.60 (4H, m, H-3, 4, 7, 8), 6.83-7.36 (9H, m, aromatic, CONH), 11.99 (1H, s, OH)

MS (TSP): m/z=518 (M+H)

Example 46

(2R,3R,4S,7S)-7-(5-Chlorosalicyl)amino-2-benzyl-5,9-dioxa-3-isobutyryloxy-4-methyl-1,6-cyclononanedione The title compound (yield 60%) was obtained in the same manner as in Example 4, except that 5-chlorosalicylic acid was used instead of 2-hydroxynicotinic acid.

$^1$H-NMR ($CDCl_3$): δ=1.20-1.40 (9H, m, $CH\underline{(CH_3)_2}$, 4-$CH_3$), 2.50-3.00 (4H, m, $\underline{CH}(CH_3)_2$, $C_6H_5\underline{CH_2}$, H-2), 3.60 (1H, bs, H-8), 4.98-5.42 (4H, m, H-3, 4, 7, 8), 6.90-8.01 (9H, m, aromatic, CONH), 11.71 (1H, s, OH)

Example 47

(2R,3R,4S,7S)-7-(4-Methoxysalicyl)amino-2-benzyl-5,9-dioxa-3-isobutyryloxy-4-methyl-1,6-cyclononanedione The title compound (yield 37%) was obtained in the same manner as in Example 4, except that 4-methoxysalicylic acid was used instead of 2-hydroxynicotinic acid.

$^1$H-NMR ($CDCl_3$): δ=1.20-1.40 (9H, m, $CH(CH_3)_2$, 4-$CH_3$), 2.60-2.80 (2H, m, $CH(CH_3)_2$, $C_6H_5CH_2$), 2.80-3.10 (2H, m, $C_6H_5CH_2$, H-2), 3.60 (1H, bs, H-8), 3.80 (3H, s, $OCH_3$), 4.90-5.50 (4H, m, H-3, 4, 7, 8), 6.50-7.40 (8H, m, aromatic), 12.10 (1H, s, OH)

TSP-MS: m/z=514 (M+H)

Example 48

(2R,3R,4S,7S)-7-(3,5-Dinitrosalicyl)amino-2-benzyl-5,9-dioxa-3-isobutyryloxy-4-methyl-1,6-cyclononanedione The title compound (yield 98%) was obtained in the same manner as in Example 4, except that 3,5-dinitrosalicylic acid was used instead of 2-hydroxynicotinic acid.

$^1$H-NMR ($CDCl_3$): δ=1.00-1.30 (9H, m, $CH(CH_3)_2$, 4-$CH_3$), 2.50-2.70 (2H, m, $CH(CH_3)_2$, $C_6H_5CH_2$), 2.70-2.90 (2H, m, $C_6H_5CH_2$, H-2), 3.60 (1H, bs, H-8), 4.60-5.20 (4H, m, H-3, 4, 7, 8), 7.00-7.30 (5H, m, $C_6H_5CH_2$), 7.60 (1H, bs, CONH), 8.60-8.90 (2H, m, aromatic (3,5-Dinitrosalicyl))

MS (TSP): m/z=573 (M+H)

Example 49

(2R,3R,4S,7S)-7-(3-(N,N-Dimethylamino)salicyl)amino-2-benzyl-5,9-dioxa-3-isobutyryloxy-4-methyl-1,6-cyclo-nonanedione The compound (30 mg) obtained in Example 40 was dissolved in 5 mL of methanol. 40% formalin (1 mL) and 3 mg of 10% palladium-carbon were added to the solution, followed by hydrogenation at room temperature under normal pressure for 8 hr. The catalyst was then removed by filtration. The filtrate was concentrated under the reduced pressure. The residue was purified by column chromatography on silica gel (methylene chloride:ethyl acetate=3:1) to give 8.0 mg (yield 27%) of the title compound.

$^1$H-NMR ($CDCl_3$): δ=1.29-1.34 (9H, m, $CH(C_3)_2$, 4-$CH_3$), 2.60-2.73 (2H, m, $CH(CH_3)_2$, $C_6H_5CH_2$), 2.73 (6H, s, $N(CH_3)_2$), 2.92-3.00 (2H, m, $C_6H_5CH_2$, H-2), 3.60 (1H, bs, H-8), 4.90-5.50 (4H, m, H-3, 4, 7, 8), 6.88 (1H, t, J=7.6, H-4'), 7.11-7.29 (6H, m, $C_6H_5$, H-5'), 7.51 (1H, d, J=9.5, H-6'), 7.96 (1H, d, J=8.2, CONH)

MS (TSP): m/z=527 (M+H)

Example 50

(2R,3R,4S,7S)-7-(5-(N,N-Dimethylamino)salicyl)amino-2-35 benzyl-5,9-dioxa-3-isobutyryloxy-4-methyl-1,6-cyclo-nonanedione The title compound (yield 26%) was obtained in the same manner as in Example 41, except that the compound obtained in Example 43 was used instead of the compound obtained in Example 40.

$^1$H-NMR ($CDCl_3$): δ=1.20-1.40 (9H, m, $CH(CH_3)_2$, 4-$CH_3$), 2.50-2.80 (2H, m, $CH(CH_3)_2$, $C_6H_5CH_2$), 2.87 (6H, s, $N(CH_3)_2$), 2.80-3.00 (2H, m, $C_6H_5CH_2$, H-2), 3.61 (1H, bs, H-8), 4.90-5.50 (4H, m, H-3, 4, 7, 8), 6.67-7.30 (9H, m, aromatic, CONH), 11.04 (1H, s, OH)

MS (TSP): m/z=527 (M+H)

Example 51

(2R,3R,4S,7S)-7-(3,5-Diaminosalicyl)amino-2-benzyl-5,9-dioxa-3-isobutyryloxy-4-methyl-1,6-cyclononanedione The title compound (yield 30%) was obtained in the same manner as in Example 41, except that the compound obtained in Example 48 was used instead of the compound obtained in Example 40.

$^1$H-NMR ($CDCl_3$): δ=1.25-1.63 (9H, m, $CH(CH_3)_2$, 4-$CH_3$), 2.61-2.75 (2H, m, $CH(CH_3)_2$, $C_6H_5CH_2$), 2.90-3.00 (2H, m, $C_6H_5CH_2$, H-2), 3.64 (1H, bs, H-8), 4.90-5.40 (4H, m, H-3, 4, 7, 8), 7.12-7.39 (7H, m, aromatic, CONH)

MS (TSP): m/z=514 (M+H)

Example 52

(2R,3R,4S,7S)-7-(5-Formylaminosalicyl)amino-2-benzyl-5,9-dioxa-3-isobutyryloxy-4-methyl-1,6-cyclononanedione The title compound (yield 75%) was obtained in the same manner as in Example 42, except that the compound obtained in Example 44 was used instead of the compound obtained in Example 41.

$^1$H-NMR ($CDCl_3$): δ=1.22-1.34 (9H, m, $CH(CH_3)_2$, 4-$CH_3$), 2.57-2.73 (2H, m, $CH(CH_3)_2$, $C_6H_5CH_2$), 2.80-3.10 (2H, m, $C_6H_5CH_2$, H-2), 3.58 (1H, bs, H-8), 5.00-5.24 (4H, m, H-3, 4, 7, 8), 7.06-7.29 (8H, m, aromatic), 11.68 (1H, s, OH)

MS (TSP): m/z=527 (M+H)

Example 53

(2R,3R,4S,7S)-7-(3-Hydroxy-4-methoxypicolinyl)amino-2-(4-nitrobenzyl)-5,9-dioxa-3-isobutyryloxy-4-methyl-1,6-cyclononanedione UK-2A (30 mg) was dissolved in 1.5 mL of methylene chloride. The solution was cooled to −20° C. Fuming nitric acid (specific gravity 1.52) (0.3 mL) was added to the solution, and a reaction was allowed to proceed at the same temperature for 2 hr. The reaction solution was diluted with cooled methylene chloride. The diluted solution was washed with saturated aqueous sodium hydrogencarbonate and water in that order, dried over magnesium sulfate, and then concentrated under the reduced pressure to give 32 mg(yield 98%) of the title compound.

$^1$H-NMR ($CDCl_3$): δ=1.26 (6H, d, J=7.1, $CH(CH_3)_2$), 1.34 (3H, d, J=6.0, 4-$CH_3$), 2.63-2.90 (2H, m, $CH(CH_3)_2$, $CH_2C_6H_4NO_2$), 2.96-3.12 (2H, m, $CH_2C_6H_4NO_2$, H-2), 3.65 (1H, bs, H-8), 3.94 (3H, s, $OCH_3$), 4.97-5.03 (1H, m, H-4), 5.19-5.30 (3H, m, H-3, 7, 8), 6.88 (1H, d, J=4.9, H-5'), 7.31 (2H, d, J=8.3, $C_6H_4NO_2$)), 7.98 (1H, d, J=4.9, H-6'), 8.13 (2H, d, J=8.3, $C_6H_4NO_2$)), 8.60 (1H, d, J=8.2, CONH), 11.73 (1H, s, OH)

MS (TSP): m/z=560 (M+H)

Example 54

(2R,3R,4S,7S)-7-(3-Hydroxy-4-methoxypicolinyl)amino-2-(4-aminobenzyl)-5,9-dioxa-3-isobutyryloxy-4-methyl-1,6-cyclononanedione The compound (220 mg) obtained in Example 53 was dissolved in 50 mL of ethanol. 10% palladium-carbon (22 mg) was added to the solution, followed by hydrogenration at room temperature under normal pressure for 6 hr. The catalyst was removed by filtration. The filtrate was then concentrated under the reduced pressure. The residue was purified by column chromatography on silica gel (chloroform:methanol =20:1) to give 151 mg (yield 72%) of the title compound.

$^1$H-NMR ($CDCl_3$): δ=1.24 (6H, d, J=7.1, $CH(CH_3)_2$), 1.34 (3H, d, J=6.0, 4-$CH_3$), 2.50-2.70 (2H, m, $CH(CH_3)_2$, $CH_2C_6H_4NH_2$), 2.80-3.00 (2H, m, $CH_2C_6H_4NH_2$, H-2), 3.61 (1H, bs, H-8), 3.94 (3H, s, $OCH_3$), 4.90-5.10 (1H, m, H-4), 5.10-5.40 (3H, m, H-3, 7, 8), 6.58 (2H, d, J=8.2, $C_6H_4NH_2$), 6.87 (1H, d, J=5.5, H-5'), 6.91 (2H, d, J=8.2, $C_6H_4NH_2$), 7.99 (1H, d, J=5.5, H-6'), 8.59 (1H, d, J=8.2, CONH), 11.79 (1H, S, OH)

MS (TSP): m/z=530 (M+H)

Example 55

(2R,3R,4S,7S)-7-(3-Hydroxy-4-methoxypicolinyl)amino-2-(4-formylaminobenzyl)-5,9-dioxa-3-isobutyryloxy-4-methyl-1,6-cyclononanedione The compound (29 mg) obtained in Example 54 was dissolved in 1 mL of methylene chloride. Formic acid (0.5 mL) and 0.1 mL of acetic anhydride were added sequentially to the solution, and a reaction was allowed to proceed at room temperature for 30 min. The reaction solution was diluted with methylene chloride. The diluted solution was washed with water, dried over magnesium sulfate, and then concentrated under the reduced pressure. The residue was purified by column chromatography on silica gel (chloroform:methanol=10: 1) to give 14 mg (yield 46%) of the title compound.

$^1$H-NMR ($CDCl_3$): δ=1.20-1.40 (9H, m, $CH(CH_3)_2$, 4-$CH_3$), 2.60-2.80 (2H, m, $CH(CH_3)_2$, $CH_2C_6H_4NHCHO$), 2.80-3.00 (2H, m, $CH_2C_6H_4NHCHO$, H-2), 3.60 (1H, bs, H-8), 3.94 (3H, s, $OCH_3$), 4.90-5.40 (1H, m, H-3, 4, 7, 8), 6.88 (1H, d, J=5.1, H-5'), 6.97-8.64 (4H, m, $C_6H_4NHCHO$), 7.99 (1H, d, J=5.1, H-6'), 11.79 (1H, s, OH)

MS (TSP): m/z=558 (M+H)

Example 56

(2R,3R,4S,7S)-7-(3-Hydroxy-4-methoxypicolinyl)amino-2-(4-(N,N-dimethylamino)benzyl)-5,9-dioxa-3-isobutyryloxy-4-methyl-1,6-cyclononanedione The compound (30 mg) obtained in Example 54 was dissolved in 5 mL of ethanol. 40% formalin (1 mL) and 3 mg of 10% palladium-carbon were added to the solution, followed by hydrogenation at room temperature under normal pressure for 4 hr. The catalyst was then removed by filtration. The filtrate was concentrated under the reduced pressure. The residue was purified by column chromatography on silica gel (chloroform:methanol =40 : 1) to give 21 mg (yield 66%) of the title compound.

$^1$H-NMR ($CDCl_3$): δ=1.24 (6H, d, J=7.1, $CH(CH_3)_2$), 1.32 (3H, d, J=6.0, 4-$CH_3$), 2.50-2.70 (2H, m, $CH(CH_3)_2$, $CH_2C_6H_4N(CH_3)_2$), 2.80-3.00 (2H, m, $CH_2C_6H_4N(CH_3)_2$, H-2), 2.90 (6H, s, $N(CH_3)_2$), 3.60 (1H, bs, H-8), 3.94 (3H, s, $OCH_3$), 4.90-5.40 (1H, m, H-3,4,7,8), 6.64 (2H, d, J=8.8, $CH_2C_6H_4N(CH_3)_2$), 6.87 (1H, d, J=5.1, H-5'), 6.99 (2H, d, J=8.8, $CH_2C_6H_4N(CH_3)_2$), 7.99 (1H, d, J=5.1, H-6'), 8.50 (1H, d, J=8.2, CONH), 11.80 (1H, s, OH)

MS (TSP): m/z=558 (M+H)

The compounds produced in the above various examples are summarized in the following Tables 1 and 2.

TABLE 1

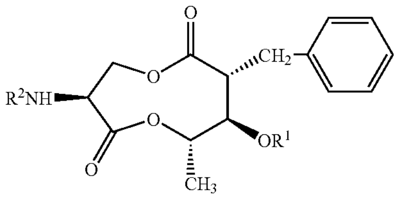

$R^1$ = $-COCH(CH_3)_2$

| Ex. | $R^2$ |
|---|---|
| 1 (1) | H |
| (2) | 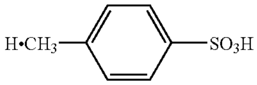 |
| 2 | 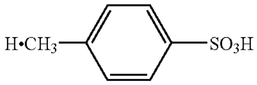 |
| 3 | 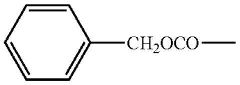 |
| 4 | 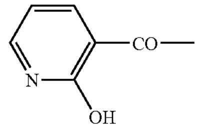 |
| 5 | 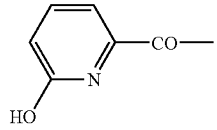 |
| 6 | 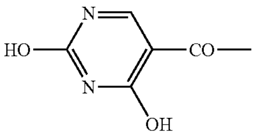 |
| 7 | 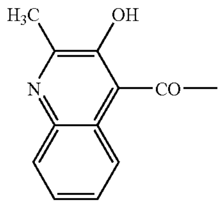 |

TABLE 1-continued
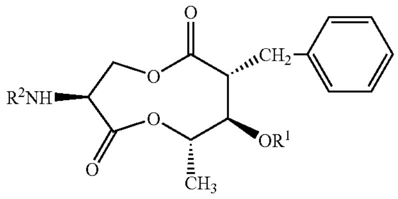
$R^1$ = -COCH(CH$_3$)$_2$
| Ex. | $R^2$ |
|---|---|
| 8 | 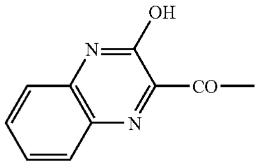 |
| 9 | 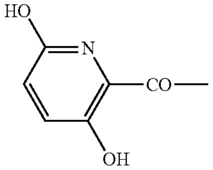 |
| 10 | 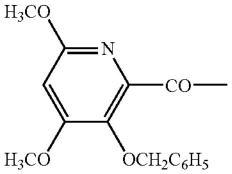 |
| 11 | 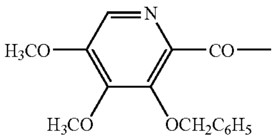 |
| 12 | 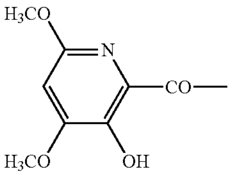 |
| 13 | 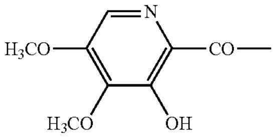 |
| 14 | 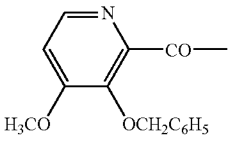 |
TABLE 1-continued
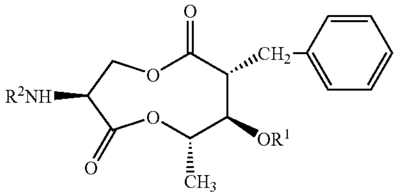
$R^1$ = -COCH(CH$_3$)$_2$
| Ex. | $R^2$ |
|---|---|
| 15 | 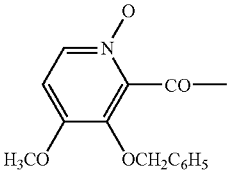 |
| 16 (1) | 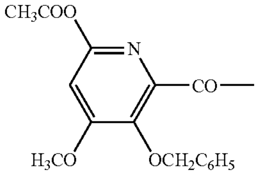 |
| (2) | 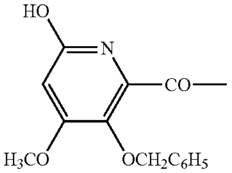 |
| 17 | 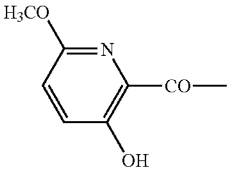 |
| 18 | 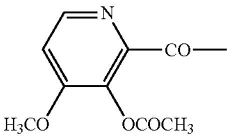 |
| 19 | 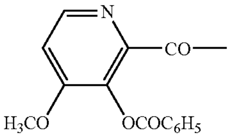 |
| 20 | 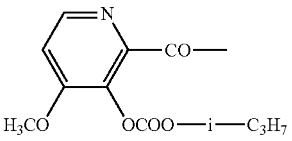 |

TABLE 1-continued
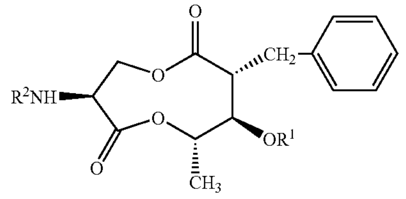
$R^1$ = -COCH(CH$_3$)$_2$
| Ex. | $R^2$ |
|---|---|
| 21 | 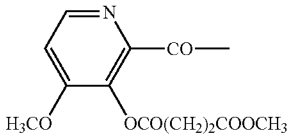 |
| 22 | 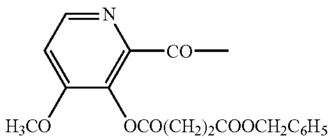 |
| 23 | 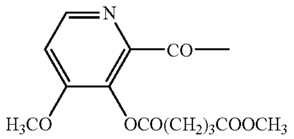 |
| 24 | 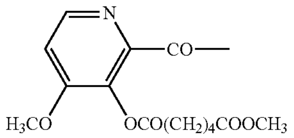 |
| 25 | 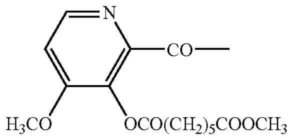 |
| 26 | 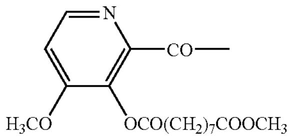 |
| 27 | 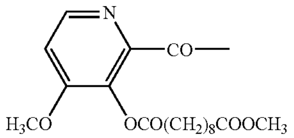 |
| 28 | 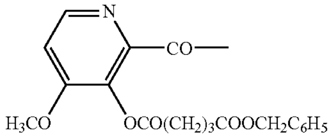 |
TABLE 1-continued
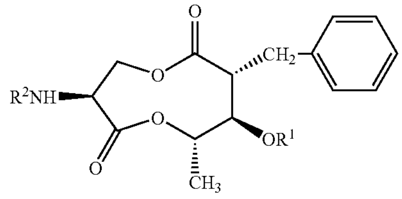
$R^1$ = -COCH(CH$_3$)$_2$
| Ex. | $R^2$ |
|---|---|
| 29 | 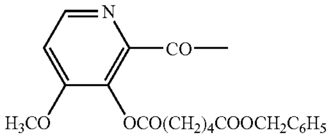 |
| 30 | 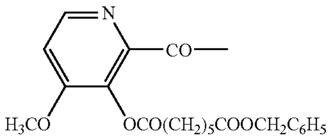 |
| 31 | 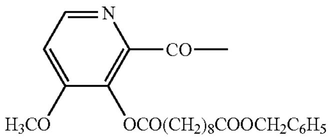 |
| 32 | 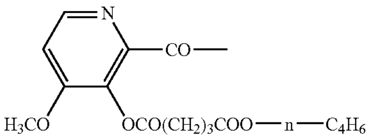 |
| 33 | 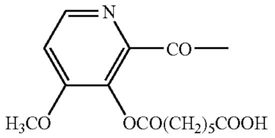 |
| 34 | 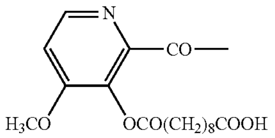 |
| 35 | 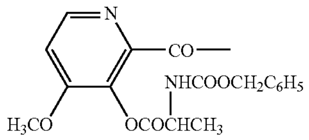 |
| 36 | 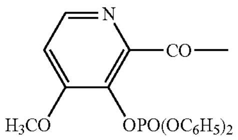 |

TABLE 1-continued
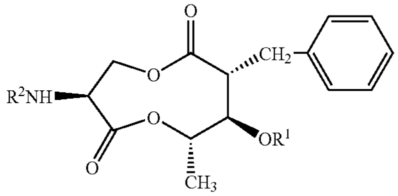
$R^1$ = -COCH$(CH_3)_2$
| Ex. | $R^2$ |
|---|---|
| 37 | 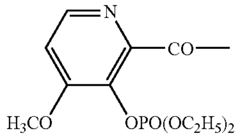 |
| 38 | 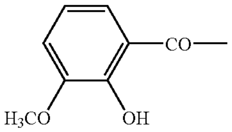 |
| 39 | 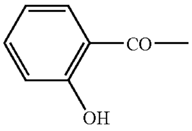 |
| 40 | 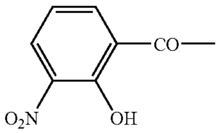 |
| 41 | 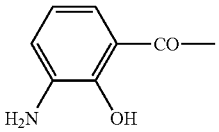 |
| 42 | 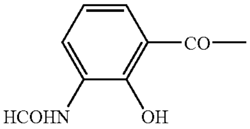 |
| 43 | 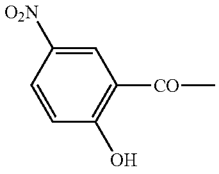 |
| 44 | 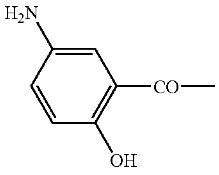 |
TABLE 1-continued
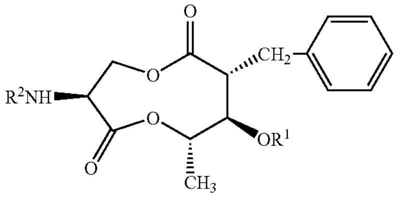
$R^1$ = -COCH$(CH_3)_2$
| Ex. | $R^2$ |
|---|---|
| 45 | 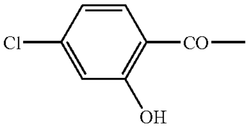 |
| 46 | 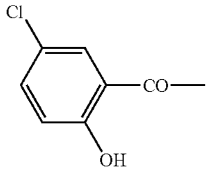 |
| 47 | 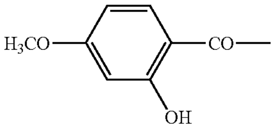 |
| 48 | 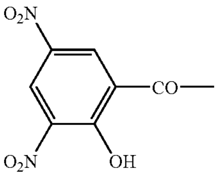 |
| 49 | 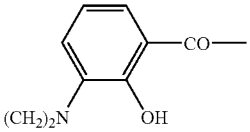 |
| 50 | 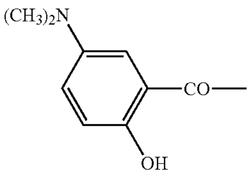 |
| 51 | 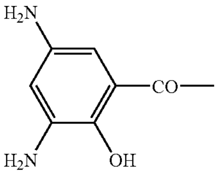 |

TABLE 1-continued

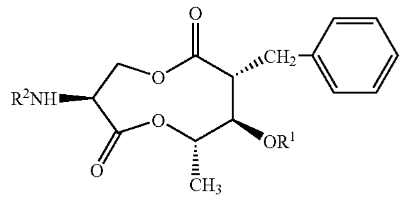

$R^1$ = -COCH($CH_3$)$_2$

| Ex. | $R^2$ |
|---|---|
| 52 | 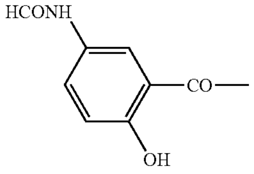 |

TABLE 2

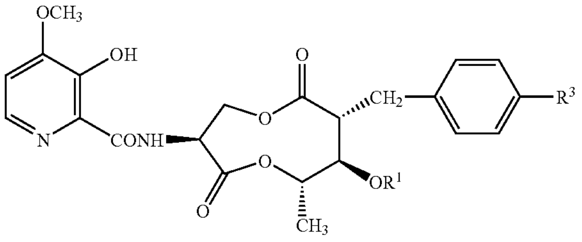

$R^1$ = —COCH($CH_3$)$_2$

| Ex. | $R^3$ |
|---|---|
| 53 | $NO_2$ |
| 54 | $NH_2$ |
| 55 | HCONH |
| 56 | $(CH_3)_2N$ |

Test Example 1

Evaluation test on antifungal activity

The antifungal activity was tested using *Saccharomyces cerevisiae* IFO 0203 by the following method.

(1) Medium

Sabouraud medium (pH 5.5-6.0)

Glucose 40 g/L

Polypeptone 10 g/L

Assay medium (pH unadjusted)

Yeast ext. (DIFCO) 10 g/L

Polypeptone 20 g/L

Glycerol 30 g/L

Bacto-agar (DIFCO) 20 g/L (2) Preparation of Assay Fungi

One platinum loop of the fungi was inoculated into the Sabouraud liquid medium (10 mL/sextant testing tube), followed by shaking cultivation at 26° C. for 24 hr (360 rpm; tube shaker).

(3) Preparation of Assay Plate

A lower layer (agar 20 g/L) was spread on an assay plate. The assay medium for an upper layer was heat melted, and then cooled to 45 to 50° C. The assay fungi (3 to 4 mL) was inoculated into 150 mL assay medium/250 mL Erlenmeyer flask. After solidification of the lower layer was confirmed, the upper layer medium was spread thereon.

(4) Evaluation of Samples

Each sample (μg) was dissolved in 25 μl of methanol to prepare evaluation samples. The evaluation samples were penetrated into a sterilized paper disk and put on the assay plate, followed by cultivation at 26° C. for one to two days to measure the inhibition zone diameter. The results are summarized in Table 3.

TABLE 3

Results of evaluation test on antifungal activity (measured value of inhibition zone diameter in mm)

| Compound | Amount of sample used, μg 0.025 | 0.05 | 0.125 | 0.25 |
|---|---|---|---|---|
| UK-2A | 19 | 22 | 26 | 26 |
| Antimycin | 12 | 14 | 16 | 18 |
| Ex. 8 | 14 | 18 | 20 | 24 |
| Ex. 17 | 16 | 19 | 24 | 27 |
| Ex. 4 | 0 | 12 | 16 | 17 |
| Ex. 39 | 8 | 8 | 11 | 12 |
| Ex. 42 | 8 | 12 | 16 | 17 |
| Ex. 49 | 8 | 8 | 12 | 14 |
| Ex. 18 | 10 | 12 | 14 | 18 |
| Ex. 21 | 15 | 19 | 22 | 25 |
| Ex. 23 | 14 | 17 | 22 | 24 |
| Ex. 28 | 11 | 13 | 15 | 18 |
| Ex. 30 | 8 | 10 | 15 | 18 |
| Ex. 33 | 12 | 16 | 21 | 24 |
| Ex. 34 | 12 | 15 | 20 | 23 |
| Ex. 35 | 12 | 17 | 22 | 26 |
| Ex. 36 | 12 | 13 | 18 | 19 |
| Ex. 53 | 12 | 15 | 18 | 20 |
| Ex. 56 | 0 | 11 | 15 | 19 |

Test Example 2

Test on plant disease protective effect (test on effect of protecting rice seedlings against blast Six three-leaf stage rice seedlings (variety:Jukkoku) raised in each of plastic pots containing compost were provided. A predetermined amount of the test compound was dissolved in acetone. Tween 20 and water were added to the solution to prepare an agent containing 10% of acetone and 0.05% of Tween 20.

This agent was applied in an amount of 10 mL per three pots by means of a spray gun. The agent was air dried. Thereafter, a conidial suspension of rice blast fungi (*Pyricularia oryzae*), which had been previously cultured in an oatmeal-agar medium, was evenly inoculated by spraying. The pots were then kept in a moist chamber at 25° C. for 24 hr. Thereafter, they were transferred to an environment control room kept at 18° C. at night and at 25° C. in the daytime to induce the disease. Seven days after the inoculation, the number of lesions which had appeared in inoculated leaves were counted. The average number of lesions per rice seedling in the treated plot was determined, and the protective value was calculated by the following equation.

The results are summarized in Table 4.

Protective value =(1- average number of lesions in treated plot/number of lesions in nontreated plot)×100

TABLE 4

Test results on the effect of protecting rice seedlings against blast

| Compound | Concentration, ppm | Protective value |
|---|---|---|
| Not applied | — | 0 |
| Rabcide sol | 100 | 100 |
| Antimycin A | 100 | 83 |
| Ex. 4 | 100 | 86 |
| Ex. 38 | 100 | 83 |
| Ex. 5 | 100 | 90 |
| Ex. 8 | 100 | 100 |
| Ex. 39 | 100 | 98 |
| Ex. 41 | 100 | 86 |

As compared with Rabcide sol currently widely used as a preventive agent for rice blast and Antimycin A known as an excellent antifungal agent, application of the novel compounds according to the present invention in the same concentration exhibited usefulness equal to or superior to that of Rabcide sol and Antimycin A. In this case, the novel compounds of the present invention do not have any phytotoxicity.

Test Example 3

Test on plant disease protective effect (test on effect of protecting cucumber against anthracic disease Cucumber seedlings (variety: Suyo) of first leaf development stage raised in each of plastic pots containing compost were provided. An agent prepared in the same manner as in Test Example 2 was applied in an amount of 5 mL per three pots by means of a spray gun. The agent was air dried. Thereafter, a conidial suspension of cucumber anthracnose fungi (Colletotricum lagenarium), which had been previously cultured in a potato soup agar medium, was evenly inoculated by spraying. The pots were then kept under moist chamber conditions at 26° C. for 24 hr to perform infection. Thereafter, they were transferred to an environment control room kept at 18° C. at night and at 25° C. in the daytime to induce the disease. Seven days after the inoculation, disease on the blade of the leaf was evaluated based on a disease index in terms of the percentage lesion area [0 (not diseased) to 5 (not less than 75% of the leaf area diseased)], and the incidence of disease and the protective value were calculated by the following equations.

The results are summarized in Table 5.

Incidence of disease =Σ(number of disease for each severity×index)/(5×number of investigated leaves)×100

Protective value =(1−incidence of disease in treated plot/number of lesions in nontreated plot)×100

TABLE 5

Test results on effect of protecting cucumber against anthracic disease

| Compound | Concentration, ppm | Protective value |
|---|---|---|
| Not applied | — | 0 |
| Antimycin A | 200 | 17 |
| Ex. 8 | 200 | 100 |
| Ex. 41 | 200 | 100 |
| Ex. 46 | 200 | 100 |

As compared with Antimycin A known as having high antifungal activity, the novel compounds according to the present invention, when applied in the same concentration, exhibited distinct superiority in antifungal activity. In this case, the novel compounds of the present invention do not have any phytotoxicity.

Test Example 4

Test on Plant Disease Protective Effect (test on Effect of Protecting Cucumber Against Downy Mildew Cucumber seedlings (variety: Suyo) of first leaf development stage raised in each of plastic pots containing compost were provided. An agent prepared in the same manner as in Test Example 2 was applied in an amount of 5 mL per three pots by means of a spray gun. The agent was air dried. Thereafter, a conidial suspension, which had been previously prepared by scraping lesion portions on the undersurface of cucumber suffering from cucumber downy mildew (pathogenic fungi: Peseudoperonocpora cubensis), was evenly inoculated by spraying. The pots were then kept under moist chamber conditions at 20° C. for 24 hr to perform infection. Thereafter, they were transferred to an environment control room kept at 18° C. at night and at 22° C. in the daytime to induce the disease. Seven days after the inoculation, disease on the blade of the leaf was evaluated based on a disease index in terms of the percentage lesion area [0 (not diseased) to 5 (not less than 75% of the leaf area diseased)], and the incidence of disease and the protective value were calculated by the following equations. The results are summarized in Table 6.

Incidence of disease =Σ(number of disease for each severity×index)/(5×number of investigated leaves)×100 Protective value =(1−incidence of disease in treated plot/number of lesions in nontreated plot)×100

TABLE 6

Test results on effect of protecting cucumber against downy mildew

| Compound | Concentration, ppm | Protective value |
|---|---|---|
| Not applied | — | 0 |
| Daconil | 50 | 78 |
| Ex. 4 | 200 | 78 |
| Ex. 5 | 200 | 100 |
| Ex. 40 | 200 | 100 |
| Ex. 41 | 200 | 88 |
| Ex. 52 | 200 | 100 |

The novel compounds according to the present invention do not have any phytotoxicity, even when they were applied at a concentration of 200 ppm, and had high protective values.

Test Example 5

Test on Plant Disease Protective Effect (Confirmation Test on Persistence of the Effect of Protecting Cucumber Against Anthracnose)

Cucumber seedlings (variety: Suyo) of first leaf development stage raised in each of plastic pots containing compost were provided. An agent prepared in the same manner as in Test Example 2 was applied in an amount of 5 mL per three pots by means of a spray gun. The agent was air dried. On the same day or 24 hr after the air drying, a conidial suspension of cucumber anthracnose fungi (Colletotricum lagenarium), which had been previously cultured in a potato soup agar medium, was evenly inoculated by spraying.

For comparison of the residual effect of protecting cucumber against anthracnose, the following three conditions (experimental plots) were set, and the incidence of disease and the protective value were calculated in the same manner as in Test Example 3. The results are summarized in Table 7.

Experimental Plots:

Plot 1: Plot subjected to inoculation on the same day as application: Inoculation was carried out on the same day as the air drying, and the pots were allowed to stand under moist chamber conditions at 26° C. for 24 hr and then allowed to stand for 7 days in an environment control room kept at 18° C. at night and at 25° C. in the daytime.

Plot 2: Plot subjected to inoculation on the day subsequent to holding under fluorescent lamp: After the air drying, the pots were placed in an environment control room under an indoor fluorescent lamp (the control room being kept at 18° C. at night and at 25° C. in the daytime with the fluorescent lamp being turned on for 8 hr in the daytime). 24 hr after the application of the agent, inoculation was carried out. Thereafter, the pots were allowed to stand under moist chamber conditions at 26° C. for 24 hr and then allowed to stand for 7 days in an environment control room kept at 18° C. at night and at 25° C. in the daytime.

Plot 3: Plot subjected to inoculation on the day subsequent to holding under sunlight: After the air drying, the pots were placed outdoors under sunlight in the daytime (8 hr) and then allowed to stand in an environment control room kept at 18° C. 24 hr after the application of the agent, inoculation was carried out. Thereafter, the pots were allowed to stand under moist chamber conditions at 26° C. for 24 hr and then allowed to stand for 7 days in an environment control room kept at 180C at night and at 25° C. in the daytime.

TABLE 7

Test results on persistence of the effect of protecting cucumber against anthracnose

| Compound | Concentration, ppm | Protective value | | |
|---|---|---|---|---|
| | | Plot 1 | Plot 2 | Plot 3 |
| UK-2A | 10 | 80 | 93 | 27 |
| | 30 | 100 | 100 | 60 |
| Ex. 18 | 10 | 67 | 93 | 60 |
| | 30 | 67 | 93 | 80 |
| | 100 | 87 | 93 | 93 |

The results show that, in the plots 1 and 2, there was no significant difference in protective value between UK-2A and the compound of Example 18, whereas, for the residual effect under sunlight which is most important for practical use (plot 3), the compound of Example 18 was much superior to UK-2A.

Test Example 6

Photostability Test (Percentage Residue as Determined by HPLC)

In consideration of use in agricultural chemicals, the following test was carried out to obtain data on photostability against exposure to sunlight.

Date and Time of Test:

First: 5 hr from 12:00 to 17:00 on May 26, 1997

Second: 6 hr from 10:00 to 16:00 on May 28, 1997

Place: For both tests, Odawara-shi, Kanagawa

Weather: For both tests, fine

Preparation of samples: UK-2A (25 mg) and the compound of Example 18 (25 mg) each were dissolved in 5 mL of acetone and then spread on a laboratory dish having a diameter of about 9 cm. Acetone was shortly evaporated. As a result, each sample was brought into a white thin film. The films thus obtained were exposed to sunlight.

After the completion of exposure to sunlight, the residual amount of UK-2A and the residual amount of the compound of Example 18 were quantitatively determined by HPLC (column: YMC-PACKODS-AS-56.0×150 mm (A-312)), mobile phase: acetonitrile-water=70 : 30 (v/v), detection wavelength: 254 nm). The results were as summarized in Table 8.

TABLE 8

Residual amount (%) of UK-2A and compound of Example 18 after exposure to sunlight

| | UK-2A | Ex. 18 |
|---|---|---|
| First test | 33 | 98 |
| Second test | 64 | 93 |

For UK-2A, it was demonstrated that O-acetylation of the hydroxyl group at the 3-position markedly improved the photostability. This fact supports the results of the test on persistence of the effect of protecting cucumber against anthracnose in Test Example 5.

Test Example 7

Photostability Test (Effect of Protecting Rice Seedlings Against Blast)

Rice seedlings of three-leaf stage (variety: Koshihikari) raised outdoors in an upland field bed (1 m×1 m) for rice seedlings were covered with a vinyl tunnel, only at night, with ears of rice suffering from blast being suspended (height 40 cm) to infect rice seedlings with blast. After the incipient infection was confirmed, agent solutions having an agent concentration of 200 ppm prepared by varying the agent concentration by the method as described in Test Example 2 each were applied in an amount of 100 mL per $m^2$ by means of a sprayer. For one week after the application of the agent, the rice seedlings were covered with the vinyl tunnel at night to promote the infection. 19 days after the application of the agent, the lesion area of the leaf was measured, and the protective value was calculated by the following equation. The results were as summarized in Table 9.

Protective value=(1−average lesion area of treated plot)/lesion area of untreated plot)×100

TABLE 9

Test results on protection of rice seedlings against blast

| Compound | Concentration, ppm | Protective value |
|---|---|---|
| Not applied | — | 0 |
| UK-2A | 200 | 63 |
| Ex. 18 | 200 | 95 |

There was a substantial correlation between the results obtained in this test example and the residual amount after exposure to sunlight in Test Example 6. Specifically, the test example demonstrated that, also in the test on the protection of rice seedlings against blast, for UK-2A, O-acetylation of the hydroxyl group at the 3'-position markedly improved the photostability.

The invention claimed is:

1. A compound represented by formula (I) or a salt thereof:

(I)

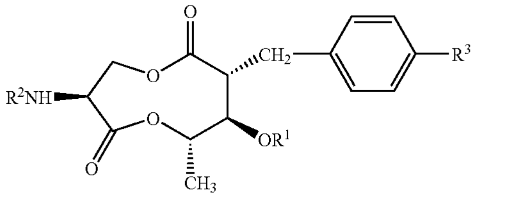

wherein $R^1$ represents isobutyryl, tigloyl, isovaleryl, or 2-methylbutanoyl;

$R^2$ represents a hydrogen atom, a benzoyl group having a substituent, or a quinoxalinoyl group having a substituent, wherein the substituent is selected from the group consisting of hydroxyl, halogen atoms, nitro, amino, di$C_{1-6}$alkylamino, formylamino, $C_{1-6}$alkyl, $C_{1-6}$alkoxy, benzyloxy, $C_{1-10}$aliphatic acyloxy, benzoyloxy, $C_{1-4}$alkyloxycarbonyloxy, ($C_{1-4}$)alkyloxycarbonyl ($C_{1-4}$)alkyloxy, p-nitrobenzyloxycarbonyl($C_{1-4}$)alkyloxy, $C_{1-6}$alkylsulfonyloxy, di($C_{1-6}$)alkylphosphoryloxy, and diphenylphosphoryloxy; and $R^3$ represents a hydrogen atom.

2. A compound represented by formula (I) or a salt thereof:

(I)

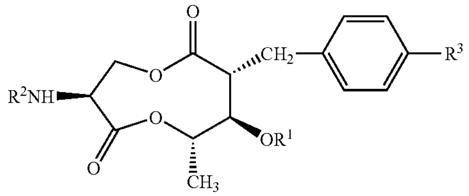

wherein $R^1$ represents isobutyryl, tigloyl, isovaleryl, or 2-methylbutanoyl;

$R^2$ represents a 3-hydroxy-4-methoxypicolinoyl group; and $R^3$ represents nitro, amino, acylamino, or N,N-dialkylamino.

3. A compound represented by formula (I) or a salt thereof:

(I)

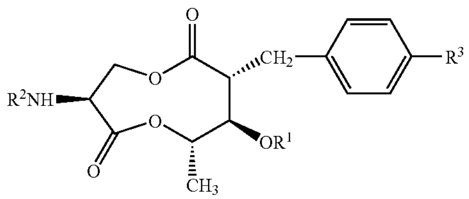

wherein $R^1$ represents isobutyryl, tigloyl, isovaleryl, or 2-methylbutanoyl;

$R^2$ represents a hydrogen atom, a benzoyl group having a substituent, a nicotinoyl group having a substituent, or a quinoxalinoyl group having a substituent, wherein the substituent is selected from the group consisting of hydroxyl, halogen atoms, nitro, amino, di$C_{1-6}$alkylamino, formylamino, $C_{1-6}$alkyl, $C_{1-6}$alkoxy, benzyloxy, $C_{1-10}$aliphatic acyloxy, benzoyloxy, $C_{1-4}$alkyloxycarbonyloxy, ($C_{1-4}$)alkyloxycarbonyl($C_{1-4}$) alkyloxy, p-nitrobenzyloxycarbonyl($C_{1-4}$)alkyloxy, $C_{1-6}$alkylsulfonyloxy, di($C_{1-6}$)alkylphosphoryloxy, and diphenylphosphoryloxy; and $R^3$ represents nitro, amino, acylamino, or N,N-dialkylamino.

4. A compound represented by formula (I) or a salt thereof:

(I)

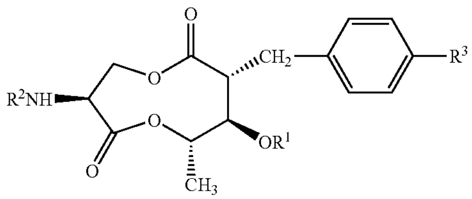

wherein $R^1$ represents isobutyryl, tigloyl, isovaleryl, or 2-methylbutanoyl;

$R^2$ represents a picolinoyl group having a substituent, wherein the substituent is selected from the group consisting of hydroxyl, halogen atoms, nitro, amino, di$C_{1-6}$alkylamino, formylamino, $C_{1-6}$alkyl, $C_{1-6}$alkoxy, benzyloxy, $C_{1-10}$oaliphatic acyloxy, benzoyloxy, $C_{1-4}$alkyloxycarbonyloxy, ($C_{1-4}$)alkyloxycarbonyl ($C_{1-4}$)alkyloxy, p-nitrobenzyloxycarbonyl($C_{1-4}$)alkyloxy, $C_{1-6}$alkylsulfonyloxy, di($C_{1-6}$)alkylphosphoryloxy, and diphenylphosphoryloxy; and $R^3$ represents nitro, amino, acylamino, or N,N-dialkylamino.

5. A compound represented by formula (I) or a salt thereof:

(I)

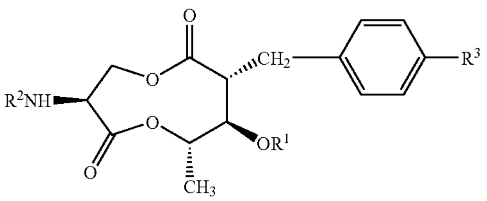

wherein $R^1$ represents isobutyryl, tigloyl, isovaleryl, or 2-methylbutanoyl;

$R^2$ represents a picolinoyl group, the 3-position of said picolinoyl group being substituted by acyloxy and the 4-position of said picolinoyl group being substituted by methoxy; and $R^3$ represents a hydrogen atom.

6. The compound or salt thereof according to claim 4, wherein $R^2$ is a picolinoyl group, said picolinoyl group being substituted by at least one substituent selected from the group consisting of hydroxy, $C_{1-6}$ alkoxy, benzyloxy, $C_{1-6}$ alkylcarbonyloxy, benzoyloxy, $C_{1-6}$ alkoxycarbonyloxy, $C_{1-6}$alkyloxycarbonyl $C_{1-10}$alkylcarbonyloxy, benzyloxycarbonyl $C_{1-10}$alkylcarbonyloxy, carboxy $C_{1-10}$ alkylcarbonyloxy, $C_{1-6}$ alkylphosphoryloxy, di($C_{1-6}$) alkylphosphoryloxy, and diphenylphosphoryloxy.

7. The compound or salt thereof according to claim 4, wherein $R^2$ is a picolinoyl group, said picolinoyl group being substituted by $C_{1-6}$ alkoxy and by at least one substituent selected from the group consisting of hydroxy, $C_{1-6}$ alkylcarbonyloxy, benzoyloxy, $C_{1-6}$ alkoxycarbonyloxy, $C_{1-6}$ alkyloxycarbonyl $C_{1-10}$alkylcarbonyloxy, benzyloxycarbonyl $C_{1-10}$ alkylcarbonyloxy, carboxy $C_{1-10}$ alkylcarbonyloxy, $C_{1-6}$ alkylphosphoryloxy, di($C_{1-6}$)alkylphosphoryloxy, and diphenylphosphoryloxy.

8. The compound or salt thereof according to claim 4, wherein $R^2$ is a picolinoyl group, the 4-position of said picolinoyl group being substituted by $C_{1-6}$ alkoxy, the 3-position of said picolinoyl group being substituted by hydroxy, $C_{1-6}$ alkylcarbonyloxy, benzoyloxy, $C_{1-6}$ alkoxycarbonyloxy, $C_{1-6}$ alkyloxycarbonyl, $C_{1-10}$ alkylcarbonyloxy, benzyloxycarbonyl $C_{1-10}$ alkylcarbonyloxy, carboxy $C_{1-10}$ alkylcarbonyloxy, $C_{1-6}$ alkylphosphoryloxy, di($C_{1-6}$) alkylphosphoryloxy, or diphenylphosphoryloxy.

9. The compound or salt thereof according to any one of claims 2, 3 or 4, wherein the acylamino represented by $R^3$ is $C_{1-6}$ acylamino or the N,N-dialkylamino represented by $R^3$ is N,N-di($C_{1-4}$)alkylamino.

10. The compound or salt thereof according to any one of claims 2, 3 or 4, wherein the acylamino represented by $R^3$ is formylamino or the N,N-dialkylamino represented by $R^3$ is N,N-dimethylamino.

11. The compound or salt thereof according to claim 4, wherein the $C_{1-6}$ alkoxy is methoxy.

12. An antifungal composition for agricultural and gardening applications comprising the compound or a salt thereof according to any one of claims 1, 2, 3 or 4 and a carrier.

13. A method for preventing the appearance and proliferation of *Pyricularia oryzae, Colletotricum lagenarium* or *Pseudoperonocpora cubensis*, comprising applying an effective amount of the compound or salt thereof according to any one of claims 1, 2, 3 or 4 to agricultural or garden plants, an environment for growing the plants, or equipment for agricultural and gardening applications.

14. A method for exterminating *Pyricularia oryzae, Colletotricum lagenarium* or *Pseudoperonocpora cubensis*, comprising using an effective amount of the compound or salt thereof according to any one of claims 1, 2 or 3 for agricultural or garden plants.

15. A method for exterminating *Pyricularia oryzae, Colletotricum lagenarium* or *Pseudoperonocpora cubensis*, comprising applying an effective amount of the compound or salt thereof according to any one of claims 1, 2 or 3 to industrial products or in the course of production of industrial products.

16. A method for treating fungal infectious diseases, comprising applying an effective amount of the compound or salt thereof according to any one of claims 1, 2, 3 or 4 to agricultural or garden plants.

17. A process for producing a compound represented by formula (I)

(I)

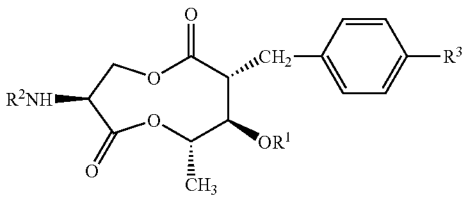

wherein $R^1$ represents isobutyryl, tigloyl, isovaleryl, or 2-methylbutanoyl, and $R^2$ and $R^3$ each independently represent a hydrogen atom, said process comprising the steps of:

chlorinating a compound represented by formula (II):

(II)

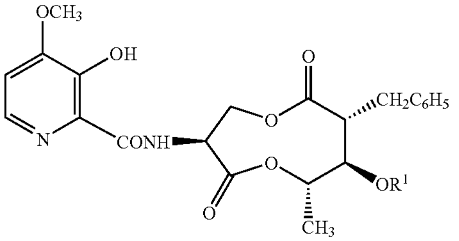

wherein $R^1$ represents isobutyryl, tigloyl, isovaleryl, or 2-methylbutanoyl, with a chlorinating agent;

etherifying the resultant imino chloro compound with an alcohol; and hydrolyzing the etherification product with water.

* * * * *